US012004708B2

(12) United States Patent
Crowley et al.

(10) Patent No.: US 12,004,708 B2
(45) Date of Patent: Jun. 11, 2024

(54) INSERTION SHEATH FOR MODULAR DISPOSABLE ENDOSCOPE COMPONENTS

(71) Applicant: GYRUS ACMI, INC., Westborough, MA (US)

(72) Inventors: Peter J. Crowley, Norfolk, MA (US); Kurt G. Shelton, Bedford, MA (US); Thomas J. Holman, Princeton, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 51 days.

(21) Appl. No.: 17/241,212

(22) Filed: Apr. 27, 2021

(65) Prior Publication Data

US 2021/0338045 A1 Nov. 4, 2021

Related U.S. Application Data

(60) Provisional application No. 63/017,901, filed on Apr. 30, 2020.

(51) Int. Cl.
*A61B 1/00* (2006.01)
*A61B 1/005* (2006.01)
(Continued)

(52) U.S. Cl.
CPC ...... *A61B 1/00066* (2013.01); *A61B 1/00006* (2013.01); *A61B 1/00016* (2013.01);
(Continued)

(58) Field of Classification Search
CPC ............ A61B 1/00066; A61B 1/00006; A61B 1/00016; A61B 1/00105; A61B 1/0011;
(Continued)

(56) References Cited

U.S. PATENT DOCUMENTS 4,660,982 A 4/1987 Okada
4,862,872 A 9/1989 Yabe et al.
(Continued)

FOREIGN PATENT DOCUMENTS

CA 2798716 A1 6/2013
CA 3068554 A1 1/2019
(Continued)

OTHER PUBLICATIONS

"U.S. Appl. No. 17/126,965, Restriction Requirement dated Sep. 30, 2022", 12 pgs.
(Continued)

*Primary Examiner* — Timothy J Neal
(74) *Attorney, Agent, or Firm* — Schwegman Lundberg & Woessner, P.A.

(57) ABSTRACT

A modular endoscope system comprises an exoskeleton, a camera unit couplable to the exoskeleton, a therapeutic unit couplable to the exoskeleton, a steering unit couplable to the exoskeleton, and a control unit couplable to the exoskeleton. A method for building a modular endoscope comprises determining camera and therapeutic capabilities of the endoscope, selecting an exoskeleton for the endoscope, attaching a camera unit and therapeutic unit, if such capabilities are determined, to the selected exoskeleton to satisfy the determined capabilities, and attaching a control unit to the exoskeleton to control any camera unit and therapeutic unit attached to the exoskeleton. A method of processing modular endoscope components for performing a surgical procedure comprises identifying a patient to receive a treatment, selecting components of the endoscope to perform the treatment, treating the patient with the endoscope, and deconstructing the components of the endoscope into reusable and disposable components.

37 Claims, 20 Drawing Sheets

(51) Int. Cl.
*A61B 1/06* (2006.01)
*A61B 1/015* (2006.01)
*A61B 1/05* (2006.01)
*A61B 1/273* (2006.01)
*A61B 18/00* (2006.01)
*A61B 18/02* (2006.01)

(52) U.S. Cl.
CPC ........ *A61B 1/00105* (2013.01); *A61B 1/0011* (2013.01); *A61B 1/00128* (2013.01); *A61B 1/0052* (2013.01); *A61B 1/0057* (2013.01); *A61B 1/06* (2013.01); *A61B 1/015* (2013.01); *A61B 1/051* (2013.01); *A61B 1/2736* (2013.01); *A61B 2018/00577* (2013.01); *A61B 2018/00595* (2013.01); *A61B 2018/00601* (2013.01); *A61B 18/02* (2013.01); *A61B 2018/0225* (2013.01); *A61B 2217/005* (2013.01); *A61B 2218/007* (2013.01)

(58) Field of Classification Search
CPC . A61B 1/00128; A61B 1/0052; A61B 1/0057; A61B 1/06; A61B 1/015; A61B 1/051; A61B 1/2736; A61B 18/02; A61B 2018/00577; A61B 2018/00595; A61B 2018/00601; A61B 2018/0225; A61B 2217/005; A61B 2218/007; A61B 1/00071; A61B 1/00101; A61B 1/00135
See application file for complete search history.

(56) References Cited

U.S. PATENT DOCUMENTS

| | | | |
|---|---|---|---|
| 5,193,525 | A | 3/1993 | Silverstein et al. |
| 5,489,256 | A | 2/1996 | Adair |
| 6,459,926 | B1 | 10/2002 | Nowlin et al. |
| 8,608,649 | B2 * | 12/2013 | McWeeney ............... A61B 1/04 600/149 |
| 9,198,719 | B2 | 12/2015 | Murdeshwar et al. |
| 11,445,890 | B2 | 9/2022 | Levinson |
| 2002/0165444 | A1 | 11/2002 | Whitman |
| 2003/0060681 | A1 * | 3/2003 | Yokota ................. A61B 1/0004 600/117 |
| 2003/0073955 | A1 | 4/2003 | Otawara |
| 2003/0191509 | A1 * | 10/2003 | Flynn .................... G16H 40/40 607/60 |
| 2006/0149127 | A1 * | 7/2006 | Seddiqui ............. A61B 1/0052 600/104 |
| 2006/0217594 | A1 | 9/2006 | Ferguson |
| 2007/0173695 | A1 | 7/2007 | Hirata |
| 2008/0091065 | A1 | 4/2008 | Oshima et al. |
| 2011/0245602 | A1 * | 10/2011 | Brannon ................ A61B 1/018 600/104 |
| 2011/0313428 | A1 | 12/2011 | Mohr et al. |
| 2012/0232345 | A1 | 9/2012 | Levy et al. |
| 2014/0187856 | A1 * | 7/2014 | Holoien ................. G16H 30/40 600/103 |
| 2014/0276101 | A1 * | 9/2014 | Asselin ................ A61B 5/4887 600/407 |
| 2015/0031946 | A1 * | 1/2015 | Saadat ................. A61B 1/0623 600/104 |
| 2015/0031947 | A1 | 1/2015 | Kudo et al. |
| 2016/0235279 | A1 * | 8/2016 | Yamakawa .......... A61B 1/3132 |
| 2017/0056102 | A1 * | 3/2017 | Germain ............ A61B 18/1485 |
| 2017/0135560 | A1 * | 5/2017 | Elia .................... A61B 1/00068 |
| 2017/0224194 | A1 | 8/2017 | Fujitani et al. |
| 2017/0280975 | A1 | 10/2017 | Levy et al. |
| 2017/0325669 | A1 | 11/2017 | Levy |
| 2018/0160888 | A1 | 6/2018 | Bunch et al. |
| 2018/0235440 | A1 | 8/2018 | Okamoto |
| 2019/0059703 | A1 | 2/2019 | Ting |
| 2021/0093166 | A1 * | 4/2021 | Shin .................... A61B 1/0052 |
| 2021/0186307 | A1 | 6/2021 | Doyle et al. |
| 2021/0196110 | A1 * | 7/2021 | Uram .................... A61B 1/07 |
| 2022/0240760 | A1 * | 8/2022 | Zhang ................ A61B 1/00128 |

FOREIGN PATENT DOCUMENTS

| | | |
|---|---|---|
| CN | 114845619 A | 8/2022 |
| CN | 115734739 A | 3/2023 |
| EP | 1302151 B1 | 5/2005 |
| EP | 3245930 A1 | 11/2017 |
| JP | 2745233 B2 | 4/1998 |
| JP | 2746651 B2 | 5/1998 |
| JP | 2750612 B2 | 5/1998 |
| JP | 2750613 B2 | 5/1998 |
| JP | 2758435 B2 | 5/1998 |
| JP | 2787471 B2 | 8/1998 |
| JP | 2802952 B2 | 9/1998 |
| JP | 2813366 B2 | 10/1998 |
| JP | 2842698 B2 | 1/1999 |
| JP | 3207991 B2 | 9/2001 |
| JP | 3220580 B2 | 10/2001 |
| JP | 4081259 B2 | 10/2001 |
| JP | 3228618 B2 | 11/2001 |
| JP | 3230617 B2 | 11/2001 |
| JP | 3327976 B2 | 2/2002 |
| JP | 3271826 B2 | 4/2002 |
| JP | 3273071 B2 | 4/2002 |
| JP | 3274746 B2 | 4/2002 |
| JP | 3276712 B2 | 4/2002 |
| JP | 3283100 B2 | 5/2002 |
| JP | 3290006 B2 | 6/2002 |
| JP | 3304161 B2 | 7/2002 |
| JP | 3306155 B2 | 7/2002 |
| JP | 3325103 B2 | 9/2002 |
| JP | 3328044 B2 | 9/2002 |
| JP | 3349804 B2 | 9/2002 |
| JP | 3353934 B2 | 9/2002 |
| JP | 3335241 B2 | 10/2002 |
| JP | 3342140 B2 | 11/2002 |
| JP | 3349813 B2 | 11/2002 |
| JP | 3365861 B2 | 11/2002 |
| JP | 3368616 B2 | 11/2002 |
| JP | 3371385 B2 | 11/2002 |
| JP | 3376121 B2 | 11/2002 |
| JP | 3352220 B2 | 12/2002 |
| JP | 3352221 B2 | 12/2002 |
| JP | 3353932 B2 | 12/2002 |
| JP | 3379714 B2 | 12/2002 |
| JP | 3365820 B2 | 1/2003 |
| JP | 3365857 B2 | 1/2003 |
| JP | 3368569 B2 | 1/2003 |
| JP | 3387594 B2 | 1/2003 |
| JP | 3394607 B2 | 1/2003 |
| JP | 3394608 B2 | 1/2003 |
| JP | 3376076 B2 | 2/2003 |
| JP | 3376106 B2 | 2/2003 |
| JP | 3392923 B2 | 3/2003 |
| JP | 3394617 B2 | 4/2003 |
| JP | 3394633 B2 | 4/2003 |
| JP | 3402646 B2 | 5/2003 |
| JP | 3433996 B2 | 5/2003 |
| JP | 3421038 B2 | 6/2003 |
| JP | 3431374 B2 | 7/2003 |
| JP | 3450510 B2 | 7/2003 |
| JP | 3476964 B2 | 9/2003 |
| JP | 3485196 B2 | 10/2003 |
| JP | 3485644 B2 | 1/2004 |
| JP | 3485648 B2 | 1/2004 |
| JP | 3485662 B2 | 1/2004 |
| JP | 3485663 B2 | 1/2004 |
| JP | 3490540 B2 | 1/2004 |
| JP | 3497591 B2 | 2/2004 |
| JP | 3510327 B2 | 3/2004 |
| JP | 3514820 B2 | 3/2004 |
| JP | 3514840 B2 | 3/2004 |
| JP | 3514847 B2 | 3/2004 |
| JP | 3514853 B2 | 3/2004 |
| JP | 3519823 B2 | 4/2004 |
| JP | 3523666 B2 | 4/2004 |

(56) References Cited

FOREIGN PATENT DOCUMENTS

| | | | |
|---|---|---|---|
| JP | 3537180 B2 | 6/2004 | |
| JP | 3540407 B2 | 7/2004 | |
| JP | 3557280 B2 | 8/2004 | |
| JP | 3597216 B2 | 12/2004 | |
| JP | 3619554 B2 | 2/2005 | |
| JP | 3651949 B2 | 5/2005 | |
| JP | 2007289342 A | 11/2007 | |
| JP | 4296159 B2 | 7/2009 | |
| JP | 3196951 B2 | 3/2015 | |
| JP | 3219521 B2 | 12/2018 | |
| WO | WO-9315648 A1 | 8/1993 | |
| WO | WO-9315648 A1 * | 8/1993 | ......... A61B 1/00052 |
| WO | WO-2011140118 A1 | 11/2011 | |
| WO | WO-2018189230 A1 | 10/2018 | |
| WO | WO-2018221672 A1 | 12/2018 | |
| WO | WO-2019152991 A1 | 8/2019 | |
| WO | WO-2019203594 A1 | 10/2019 | |
| WO | WO-2021127703 A2 | 6/2021 | |
| WO | WO-2021127703 A3 | 7/2021 | |
| WO | WO-2021222208 A1 | 11/2021 | |

OTHER PUBLICATIONS

"International Application Serial No. PCT/US2021/029345, International Preliminary Report on Patentability dated Nov. 10, 2022", 14 pgs.

"International Application Serial No. PCT/US2020/070936, International Search Report dated Jun. 16, 2021", 8 pgs.

"International Application Serial No. PCT/US2020/070936, Invitation to Pay Additional Fees dated Apr. 21, 2021", 13 pgs.

"International Application Serial No. PCT/US2020/070936, Written Opinion dated Jun. 16, 2021", 11 pgs.

"U.S. Appl. No. 17/126,965 Preliminary Amendment filed May 9, 2022", 9 pgs.

"International Application Serial No. PCT/US2020/070936, International Preliminary Report on Patentability dated Jun. 30, 2022", 13 pgs.

"International Application Serial No. PCT/US2021/029345, Invitation to Pay Additional Fees dated Aug. 11, 2021", 14 pgs.

"International Application Serial No. PCT/US2021/029345, International Search Report dated Oct. 5, 2021", 9 pgs.

"International Application Serial No. PCT/US2021/029345, Written Opinion dated Oct. 5, 2021", 12 pgs.

"U.S. Appl. No. 17/126,965, Non Final Office Action dated Mar. 27, 2023", 20 pgs.

"U.S. Appl. No. 17/126,965, Response filed Nov. 30, 2022 to Restriction Requirement dated Sep. 30, 2022", 11 pgs.

"Chinese Application Serial No. 202080088080.4, Voluntary Amendment filed Nov. 8, 2022", w/o English Claims, 8 pgs.

"U.S. Appl. No. 17/126,965, Final Office Action dated Oct. 24, 2023", 25 pgs.

"U.S. Appl. No. 17/126,965, Response filed Jun. 27, 2023 to Non Final Office Action dated Mar. 27, 2023", 19 pgs.

"U.S. Appl. No. 17/126,965, Response filed Dec. 12, 2023 to Final Office Action mailed Oct. 24, 2023", 17 pgs.

"U.S. Appl. No. 17/126,965, Advisory Action mailed Dec. 22, 2023", 3 pgs.

"U.S. Appl. No. 17/126,965, Response filed Jan. 23, 2024 to Advisory Action mailed Dec. 22, 2023", 11 pgs.

* cited by examiner

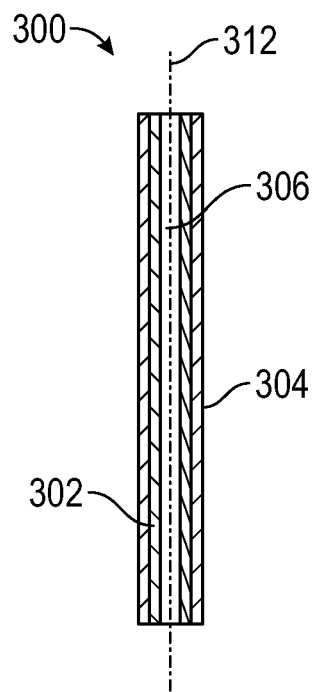 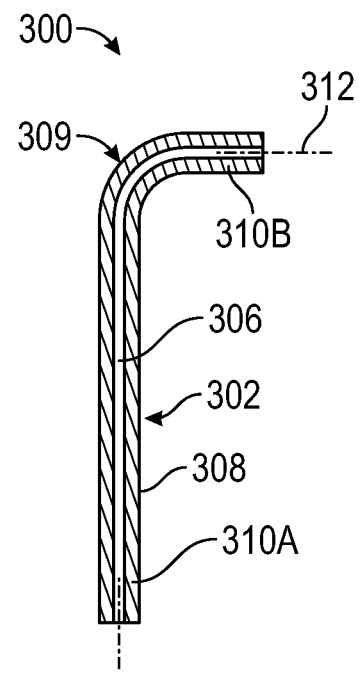
FIG. 14A        FIG. 14B
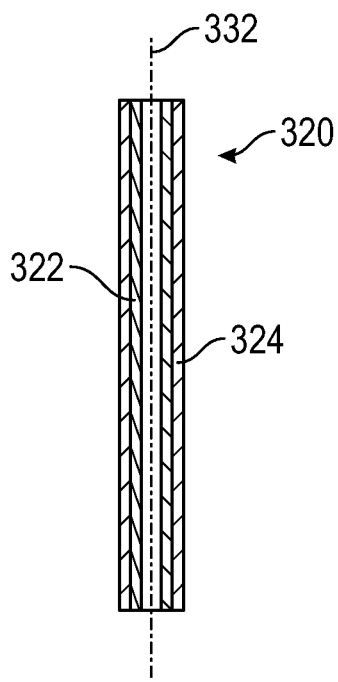 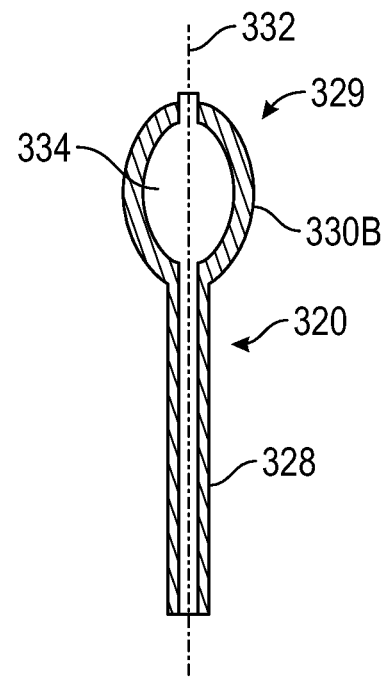
FIG. 15A        FIG. 15B

INSERTION SHEATH FOR MODULAR DISPOSABLE ENDOSCOPE COMPONENTS

CROSS-REFERENCE TO RELATED PATENT DOCUMENTS

This patent application claims the benefit of priority to U.S. provisional patent application 63/017,901 filed Apr. 30, 2020, titled "Insertion Sheath for Modular Endoscope With Detachable and Selectively Disposable Components". This patent application is also related to U.S. provisional patent application 62/958,041 filed on Jan. 7, 2020, titled "Endoscope with a Low-Profile Distal Section"; U.S. provisional patent application 62/951,157 filed on Dec. 20, 2019, titled, "Modular Endoscope with Detachable and Selectively Disposable Components;" and U.S. provisional patent application 62/958,782 filed on Jan. 9, 2020, titled, "Endoscope with an Elevator," the entire contents of which are hereby incorporated by reference.

TECHNICAL FIELD

The present disclosure relates generally to medical devices comprising elongate bodies configured to be inserted into incisions or openings in anatomy of a patient to provide diagnostic or treatment operations.

More specifically, the present disclosure relates to endoscopes for imaging and/or providing passage of therapeutic devices toward various anatomical portions, including gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

BACKGROUND

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like.

In conventional endoscopy, the distal portion of the endoscope can be configured for supporting and orienting a therapeutic device. However, such distal portions can, in a few instances, lead to difficulty in sterilizing or reprocessing the distal portion after use. For example, conventional endoscopy devices can be completely reusable such that crevices between components or spaces within functional components of the distal portion can be difficult to access and clean.

SUMMARY

As is discussed below in greater detail, the present inventors have recognized that problems to be solved with conventional medical devices, and in particular endoscopes and duodenoscopes, include, among other things, particularly those that are difficult or not configured to be easily disassembled, 1) the need and difficulty of cleaning and sterilizing endoscopes after usage, 2) the cost of maintaining multiple endoscopes in inventory to perform different surgical techniques or therapeutic methods on different patients, and 3) the cost of purchasing medical devices having excess capacity or unwanted capabilities for a particular patient. The present disclosure can help provide solutions to these and other problems by providing systems, devices and methods for designing, building, using and deconstructing modular endoscopes. In particular, the present application is directed to modular insertion sheaths, shafts and insertion modules for medical devices such as endoscopes and duodenoscopes. The insertion sheaths and shafts can be configured for one-time use. As such, more expensive components can be modularly attached to the disposable insertion sheaths and shafts. Thus, said components can be configured for cleaning, e.g., by being encapsulated, while the insertion sheath and shafts can be inexpensively made to perform only the desired procedure and then disposed of after use. Such configurations can eliminate the need to clean in difficult to reach places in fully assembled devices.

In an example, a method for building a modular endoscope can comprise determining a camera capability of the modular endoscope, determining a therapeutic capability of the modular endoscope, selecting an exoskeleton for the modular endoscope to be used with the determined camera and therapeutic capabilities of the modular endoscope, attaching a camera unit, if a camera capability is determined, to the selected exoskeleton to satisfy the determined camera capability, attaching a therapeutic unit, if a therapeutic capability is determined, to the selected exoskeleton to satisfy the determined therapeutic capability, and attaching a control unit to the exoskeleton to control any camera unit and therapeutic unit attached to the exoskeleton.

In another example, a modular endoscope system can comprise an exoskeleton, a camera unit couplable to the exoskeleton, a therapeutic unit couplable to the exoskeleton, a navigation and control unit couplable to the exoskeleton, and a control unit couplable to the exoskeleton.

In an additional example, a method of processing modular endoscope components for performing a surgical procedure can comprise identifying a specific patient to receive a specific treatment, selecting components of the modular endoscope to perform the specific treatment, treating the specific patient with the modular endoscope, and deconstructing the components of the modular endoscope into reusable and disposable components.

BRIEF DESCRIPTION OF DRAWINGS

FIGS. 14A and 14B are schematic cross-sectional view of a bendable shaft in a collapsed state and an extended state, respectively.

FIGS. 15A and 15B are schematic cross-sectional view of an expandable shaft in a collapsed state and an expanded state, respectively.

DETAILED DESCRIPTION

Figure 1:
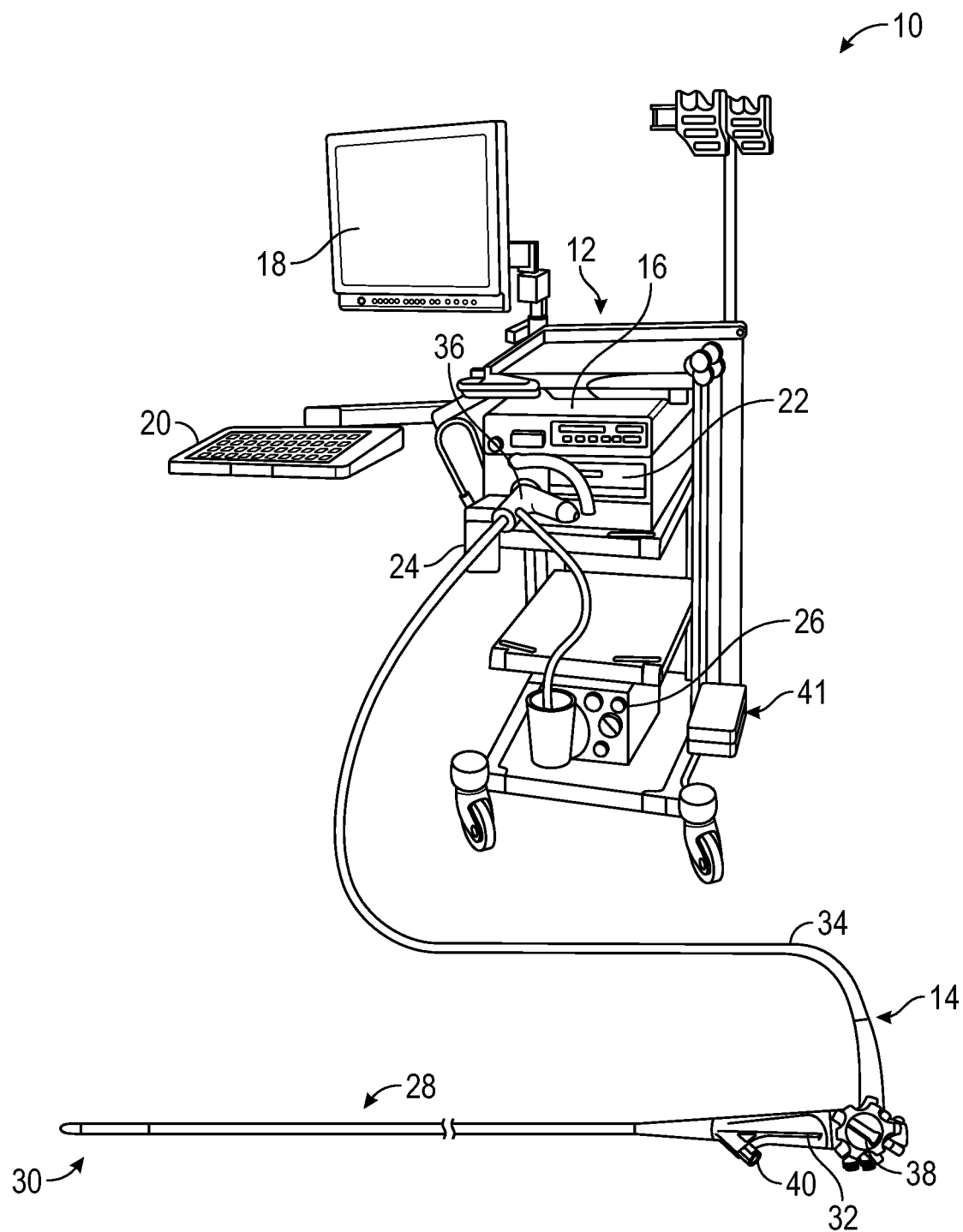
FIG. 1 is a schematic diagram of an endoscopy system comprising an imaging and control system and a duodenoscope.

FIG. 1 is a schematic diagram of endoscopy system 10 comprising imaging and control system 12 and endoscope 14. FIG. 1 an illustrative example of an endoscopy system suitable for use with the systems, devices and methods described herein, such as modular endoscopy systems, modular endoscopes and methods for designing, building and deconstructing endoscopes. According to some examples, endoscope 14 can be insertable into an anatomical region for imaging and/or to provide passage of one or more sampling devices for biopsies, or one or more therapeutic devices for treatment of a disease state associated with the anatomical region. Endoscope 14 can, in advantageous aspects, interface with and connect to imaging and control system 12. In the illustrated example, endoscope 14 comprises a duodenoscope, though other types of endoscopes can be used with the present disclosure.

Imaging and control system 12 can comprise controller 16, output unit 18, input unit 20, light source 22, fluid source 24 and suction pump 26.

Imaging and control system 12 can include various ports for coupling with endoscopy system 10. For example, controller 16 can include a data input/output port for receiving data from and communicating data to endoscope 14. Light source 22 can include an output port for transmitting light to endoscope 14, such as via a fiber optic link. Fluid source 24 can include a port for transmitting fluid to endoscope 14. Fluid source 24 can comprise a pump and a tank of fluid our can be connected to an external tank, vessel or storage unit. Suction pump 26 can comprise a port used to draw a vacuum from endoscope 14 to generate suction, such as for withdrawing fluid from the anatomical region into which endoscope 14 is inserted. Output unit 18 and input unit 20 can be used by an operator of endoscopy system 10 to control functions of endoscopy system 10 and view output of endoscope 14. Controller 16 can additionally be used to generate signals or other outputs from treating the anatomical region into which endoscope 14 is inserted. In examples, controller 16 can generate electrical output, acoustic output, a fluid output and the like for treating the anatomical region with, for example, cauterizing, cutting, freezing and the like.

Endoscope 14 can comprise insertion section 28, functional section 30 and handle section 32, which can be coupled to cable section 34 and coupler section 36.

Insertion section 28 can extend distally from handle section 32 and cable section 34 can extend proximally from handle section 32. Insertion section 28 can be elongate and include a bending section, and a distal end to which functional section 30 can be attached. The bending section can be controllable (e.g., by control knob 38 on handle section 32) to maneuver the distal end through tortuous anatomical passageways (e.g., stomach, duodenum, kidney, ureter, etc.). Insertion section 28 can also include one or more working channels that can be elongate and support insertion of one or more therapeutic tools of functional section 30. The working channel can extend between handle section 32 and functional section 30. Additional functionalities, such as fluid passages, guide wires, and pull wires can also be provided by insertion section 28 (e.g., via suction or irrigation passageways, and the like).

Handle module 32 can comprise knob 38 as well as ports 40. Knob 38 can be coupled to a pull wire extending through insertion section 28. Ports 40 can be configured to couple various electrical cables, fluid tubes and the like to handle module 32 for coupling with insertion section 28.

Imaging and control system 12, according to examples, can be provided on a mobile platform (e.g., cart 41) with shelves for housing light source 22, suction pump 26, image processing unit 42, etc. Alternatively, several components of imaging and control system 12 shown in FIGS. 1 and 2 can be provided directly on endoscope 14 so as to make the endoscope "self-contained."

Figure 2:
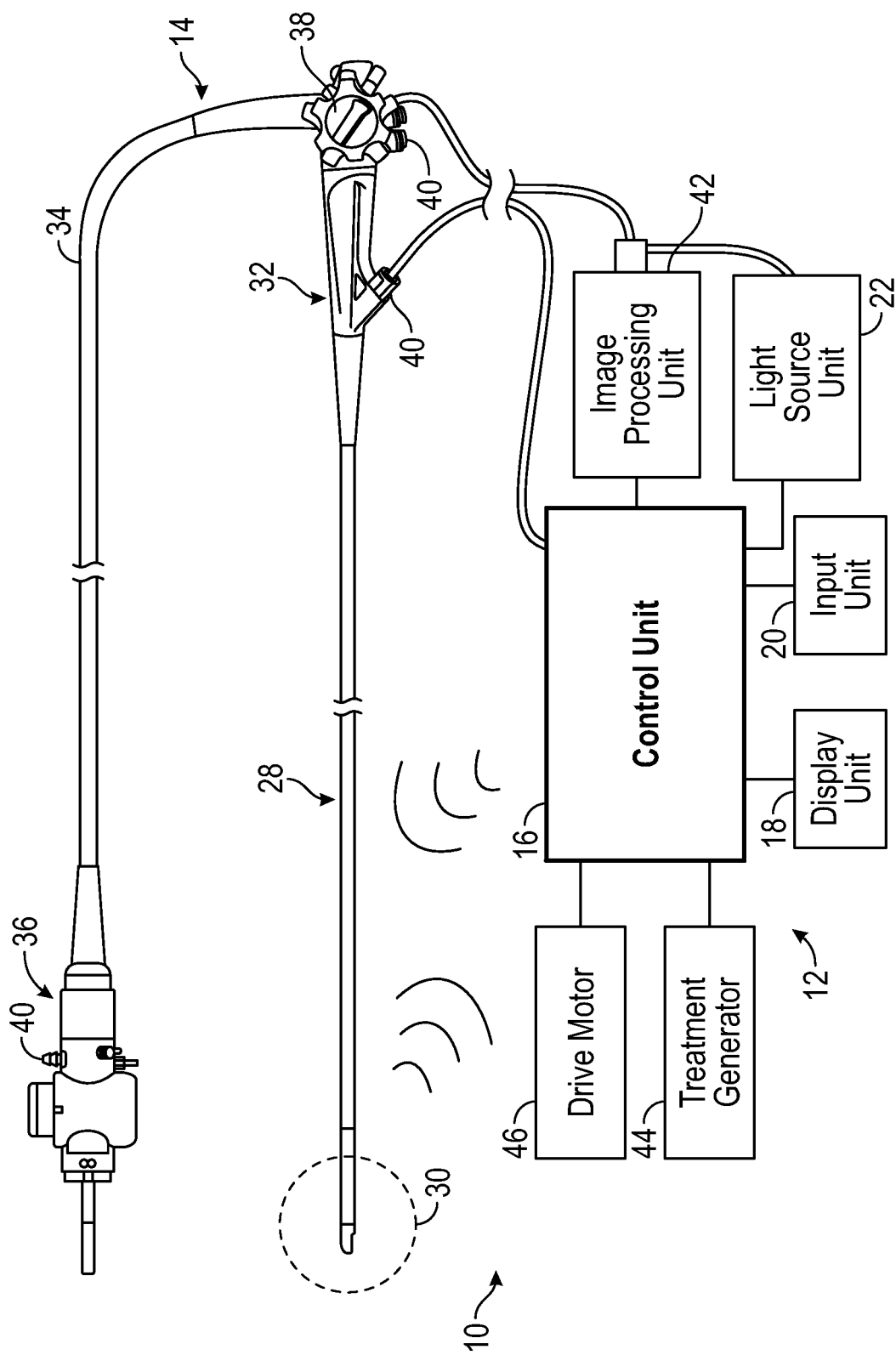
FIG. 2 is a schematic diagram of the endoscopy system of FIG. 1 comprising an endoscope and a control unit.

FIG. 2 is a schematic diagram of endoscopy system 10 of FIG. 1 comprising imaging and control system 12 and endoscope 14. FIG. 2 schematically illustrates components of imaging and control system 12 coupled to endoscope 14, which in the illustrated example comprises a duodenoscope. Imaging and control system 12 can comprise controller 16, which can include or be coupled to image processing unit 42, treatment generator 44 and drive unit 46, as well as light source 22, input unit 20 and output unit 18.

Image processing unit 42 and light source 22 can each interface with endoscope 14 by wired or wireless electrical connections. Imaging and control system 12 can accordingly illuminate an anatomical region, collect signals representing the anatomical region, process signals representing the anatomical region, and display images representing the anatomical region on a display. Imaging and control system 12 can include a light source to illuminate the anatomical region using light of desired spectrum (e.g., broadband white light, narrow-band imaging using preferred electromagnetic wavelengths, and the like). Imaging and control system 12 can connect (e.g., via an endoscope connector) to endoscope 14 for signal transmission (e.g., light output from light source, video signals from imaging system in the distal end, and the like).

Fluid source 24 can comprise one or more sources of air, saline or other fluids, as well as associated fluid pathways (e.g., air channels, irrigation channels, suction channels) and connectors (barb fittings, fluid seals, valves and the like). Imaging and control system 12 can also include drive unit 46, which can be an optional component. Drive unit 46 can comprise a motorized drive for advancing a distal section of endoscope 14, as described in at least PCT Pub. No. WO 2011/140118 A1 to Frassica et al., titled "Rotate-to-Advance Catheterization System," which is hereby incorporated in its entirety by this reference.

Figure 3A:
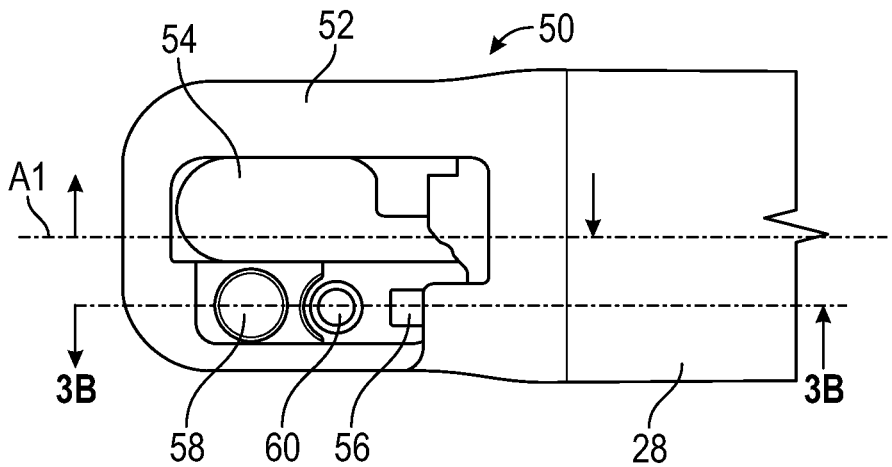
FIG. 3A is a schematic top view of a camera module including optical components for a side-viewing endoscope.
Figure 3B:
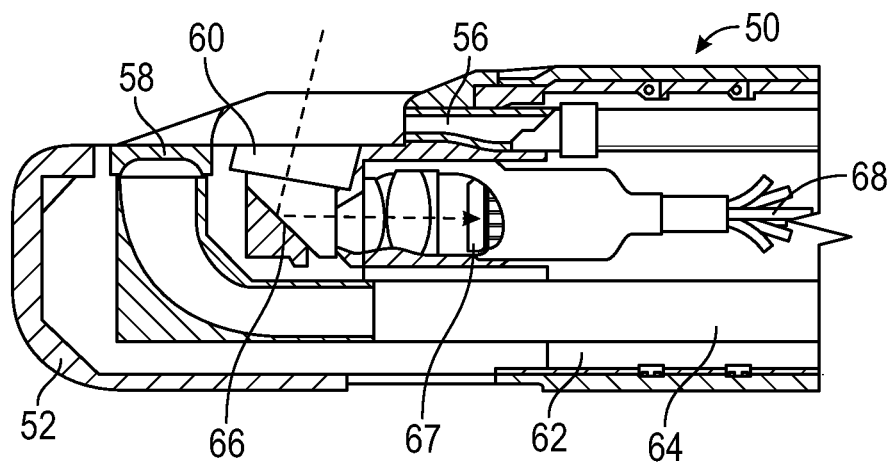
FIG. 3B is an enlarged cross-sectional view taken along the plane 3B-3B of FIG. 3A showing the optical components.

FIGS. 3A and 3B illustrate a first example of functional section 30 of endoscope 14 of FIG. 2. FIG. 3A illustrates a top view of functional section 30 and FIG. 3B illustrates a cross-sectional view of functional section 30 taken along section plane 3B-3B of FIG. 3A. FIGS. 3A and 3B each illustrate "side-viewing endoscope" (e.g., duodenoscope) camera module 50. In side-viewing endoscope camera module 50, illumination and imaging systems are positioned such that the viewing angle of the imaging system corresponds to a target anatomy lateral to central longitudinal axis A1 of endoscope 14.

In the example of FIGS. 3A and 3B, side-viewing endoscope camera module 50 can comprise housing 52, elevator 54, fluid outlet 56, illumination lens 58 and objective lens 60. Housing 52 can form a fluid tight coupling with insertion section 28. Housing 52 can comprise opening for elevator 54. Elevator 54 can comprise a mechanism for moving a device inserted through insertion section 28. In particular, elevator 54 can comprise a device that can bend an elongate device extended through insertion section 28 along axis A1. Elevator 54 can be used to bend the elongate device at an angle to axis A1 to thereby treat the anatomical region adjacent side-viewing endoscope camera module 50.

As can be seen in FIG. 3B, insertion section 28 can comprise central lumen 62 through which various components can be extended to connect functional section 30 with handle section 32 (FIG. 2). For example, illumination lens 58 can be connected to light transmitter 64, which can comprise a fiber optic cable or cable bundle extending to light source 22 (FIG. 1). Likewise, objective lens 60 can be coupled to prism 66 and imaging unit 67, which can be coupled to wiring 68. Also, fluid outlet 56 can be coupled to fluid line 69, which can comprise a tube extending to fluid source 24 (FIG. 1). Other elongate elements, e.g., tubes, wires, cables, can extend through lumen 62 to connect functional section 30 with components of endoscopy system 10, such as suction pump 26 (FIG. 1) and treatment generator 44 (FIG. 2).

Figure 4A:
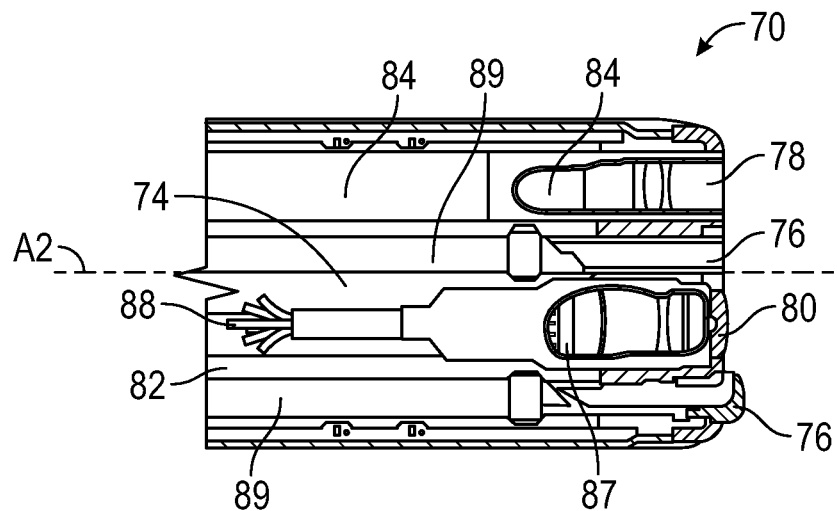
FIG. 4A is an end view of a camera module including optical components for an end-viewing endoscope.
Figure 4B:
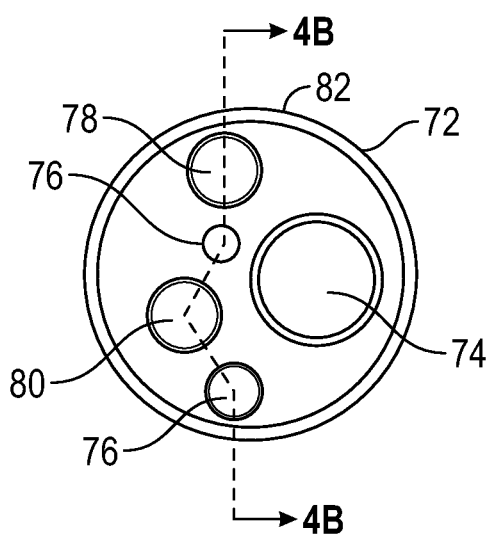
FIG. 4B is a cross-sectional view taken along the plane 4B-4B of FIG. 4A showing the optical components.

FIGS. 4A and 4B illustrate a second example of functional section 30 of endoscope 14 of FIG. 2. FIG. 4A illustrates and end view of functional section 30 and FIG. 4B illustrates a cross-sectional view of functional section 30 taken along section plane 4B-4B of FIG. 4A. FIGS. 4A and 4B each illustrate "end-viewing endoscope" (e.g., gastroscope, colonoscope, cholangioscope, etc.) camera module 70. In end-viewing endoscope camera module 70, illumination and imaging systems are positioned such that the viewing angle of the imaging system corresponds to a target anatomy located adjacent an end of endoscope 14 and in line with central longitudinal axis A2 of endoscope 14.

In the example of FIGS. 4A and 4B, end-viewing endoscope camera module 70 can comprise housing 72, therapy unit 74, fluid outlet 76, illumination lens 78 and objective lens 80. Housing 72 can comprise and endcap for insertion section 28, thereby providing a seal to lumen 82.

As can be seen in FIG. 4B, insertion section 28 can comprise lumen 82 through which various components can be extended to connect functional section 30 with handle section 32 (FIG. 2). For example, illumination lens 78 can be connected to light transmitter 84, which can comprise a fiber optic cable or cable bundle extending to light source 22 (FIG. 1). Likewise, objective lens 80 can be coupled to imaging unit 87, which can be coupled to wiring 88. Also, fluid outlets 76 can be coupled to fluid lines 89, which can comprise a tube extending to fluid source 24 (FIG. 1). Other elongate elements, e.g., tubes, wires, cables, can extend through lumen 82 to connect functional section 30 with components of endoscopy system 10, such as suction pump 26 (FIG. 1) and treatment generator 44 (FIG. 2). For example, therapy unit 74 can comprise a wide-diameter lumen for receiving other treatment components, such as cutting devices and therapeutic devices.

Both side-viewing endoscope camera module 50 of FIGS. 3A and 3B and end-viewing endoscope camera module 70 of FIGS. 4A and 4B have several elements in common. In particular, endoscope camera modules 50 and 70 can include optical components (e.g., objective lenses 60 and 80, prism 66, imaging units 67 and 87, wiring 68 and 88) for collection of image signals, lighting components (e.g., illumination lenses 58 and 78, light transmitters 64 and 84) for transmission or generation of light. Endoscope camera modules 50 and 70 can also include a photosensitive element, such as a charge-coupled device ("CCD" sensor) or a complementary metal-oxide semiconductor ("CMOS") sensor. In either example, imaging units 67 and 87 can be coupled (e.g., via wired or wireless connections) to image processing unit 42 (FIG. 2) to transmit signals from the photosensitive element representing images (e.g., video signals) to image processing unit 42, in turn to be displayed on a display such as output unit 18. In various examples, imaging and control system 12 and image processing units 67 and 87 can be configured to provide outputs at desired resolution (e.g., at least 480p, at least 720p, at least 1080p, at least 4K UHD, etc.) suitable for endoscopy procedures.

The present inventors have recognized that problems to be solved with conventional endoscopes include, among others, are 1) the need for cleaning and sterilizing endoscopes after usage and 2) the cost of maintaining multiple endoscopes in inventory to perform different surgical techniques or therapeutic methods on different patients. The present inventors have developed solutions to these and other problems by recognizing that many endoscopes and surgical devices share common components, which are a mix of inexpensive and expensive components, and simple components and complex components. As such, the present inventors have developed modular endoscopy components that can be assembled in a custom manner to perform only desired diagnostic and therapeutic procedures for a specific patient, and the disassembled to dispose of certain components and clean modular components particularly designed to be self-contained, sealed and easily cleaned. The present disclosure, in particular, describes a plurality of modular insertion sheaths and shafts that can, in many instances, comprise disposable components, and can be built to provide a platform for mounting only the desired modular functional components (e.g., camera modules, diagnostic modules and therapeutic modules).

Figure 5:
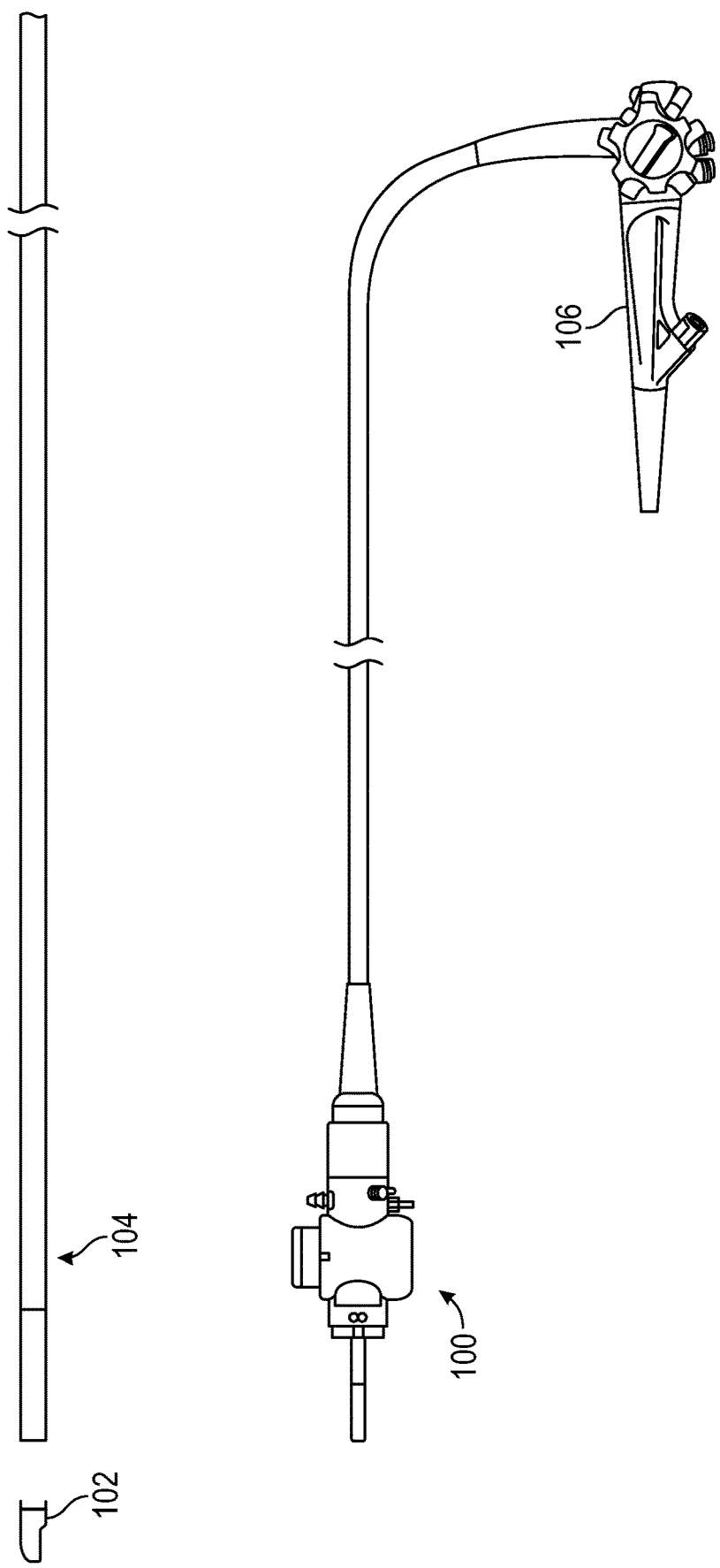
FIG. 5 is a schematic view of a modular endoscope suitable for use as the endoscope of FIGS. 1A-4B comprising a modularly detachable camera module, an insertion section module and a navigation and control module.

FIG. 5 is a schematic view of modular endoscope 100 suitable for use as endoscope 14 and with endoscope camera modules 50 and 70 of FIGS. 1-4B. Modular endoscope 100 can comprise a modular detachable functional module 102, insertion section module 104 and navigation and control module 106. Modules 102, 104 and 106 can comprise components including customizable features and components. As such, modular endoscope 100 can be custom-built to perform a specific procedure for a specific patient. Individual modular components can be configured as reusable or disposable components. Therefore, inexpensive or difficult to clean components can be disposed of and expensive or easy to clean components can be reused after appropriate cleaning and sterilizing.

Functional module 102 can comprise functional module 30 or other types of modules. Functional module 30 can include one or both of an imaging device, a therapeutic device, and an ancillary therapeutic device, as well as other devices as is described herein.

Insertion section module 104 can comprise insertion section 28, which can be configured to include one or more of the sheath and shaft components of FIGS. 6A-15B discussed below.

Navigation and control module 106 can comprise handle section 32, cable section 34 and coupler section 36 of FIGS. 1 and 2. Navigation and control module 106 can additionally comprise control unit 404 and control unit 504 of FIGS. 16A and 16B and FIGS. 17A and 17B, respectively.

As mentioned previously, components of endoscope 14 can be modular such that they can be attached by an operator to initially configure the device for use with a patient, and can be detached by the operator after use with the patient. In other examples, the modular components can be assembled and disassembled by a manufacturer or a decommissioning service without action from the operator. In an example, FIG. 5 illustrates endoscope 14 of FIG. 2, wherein components thereof are shown in a detached state. While FIG. 5 illustrates endoscope 14 as being constructed from three modular components (functional module 102 [functional section 30]), navigation and control module 106 [handle section 32], insertion section module 104 [insertion section 28]), additional or fewer components are contemplated, depending on the surgical procedure to be performed with the embodiment of endoscope 14 constructed or designed by the operator. Each of functional module 102, navigation and control module 106, and insertion section module 104 can be detachable from each other. Furthermore, each of modules 102, 104 and 106 can be disposed after a single clinical use. Alternatively, each of modules 102, 104 and 106 can be constructed using materials that would permit several clinical uses. In such cases, modules 102, 104 and 106 can be constructed to withstand sterilization after each clinical use.

In certain advantageous aspects, the modular construction of endoscope 14 of FIGS. 2 and 5, and as discussed herein, can permit mixing and matching of disposable and reusable modules such that some modules can be reused, such as expensive and/or easy to clean modules, and some modules can be disposable, such as simple and/or difficult to clean modules. For example, certain modules can be detached from the endoscope after a clinical use for sterilization, reprocessing, and reuse for subsequent clinical uses, while the remaining modules can be disposed. For instance, there have been concerns with inadequate reprocessing of portions of duodenoscopes (e.g., elevator portion, seen in FIG. 3A). As a result, single-use endoscopes that can be disposed after a single clinical use (to prevent infection between uses) have been developed. However, currently available single-use endoscopes, wherein the entire endoscope is disposed of, can be constructed using lower cost materials resulting in a lower price for the endoscope in order to remain competitive per clinical use. In many clinical instances, lower cost materials can lead to poorer clinical performance (e.g., lower quality images, inadequate maneuverability, insertion section module damage during insertion, poorer ergonomic of endoscope handle, etc.). As such, inferior components can result in practitioners preferring not to use such devices.

Accordingly, modular endoscope 14 of FIGS. 2 and 5, and other described herein, is advantageously constructed such that the end user (e.g., health care providers and facilities) can recover certain modules of endoscope 14 for reuse, while disposing infection prone areas after a single clinical use. In addition, portions of the endoscope that are intended for reuse can be constructed to reduce accumulation of biological materials (such as be being fully encapsulated), and can additionally be fluidly isolated from infection prone areas. Such configurations promote the use of a combination of higher quality (higher cost) reusable components usable over multiple clinical uses, and lower cost, disposable portions, while reducing infection risk, and achieving desired clinical performance. Not only can the disposable components be constructed to include features only needed for the specifically-built procedure, but the materials and construction can be built to only survive one-time use, both of which help reduce the cost of the disposable components.

In examples, endoscope 100 of FIG. 5 can comprise a duodenoscope, functional module 102 can be configured as a reusable camera module, navigation and the control module 106 can comprise a reusable handle module, and insertion section module 104 can comprise a disposable unit having multiple lumens. Accordingly, the camera module and the navigation and control module can each include connectors that can maintain each of the camera module and the navigation and control module in an attached state to the insertion section module during use with a patient. After each use, the camera module and the navigation and control module can be separated (e.g., using the connectors), and reprocessed for subsequent use with a new insertion section module. Conversely, the used insertion section module can be disposed after a single use.

Additionally, the connectors of the camera module and the navigation and the control module as well as the camera module and the navigation and the control module can be constructed of materials and engineered to reduce any ingress of biological materials and may optionally be constructed in a fluid-tight manner.

Modular endoscope 100 can be configured for either a "side-viewing" configuration (as shown in FIGS. 3A-3B) or an "end-viewing" configuration (as shown in FIGS. 4A-4B). In examples, wherein modular endoscope 100 is configured as a side-viewing device (e.g., side-viewing duodenoscope), the distal modular section (e.g., camera module) can be offset from a longitudinal axis of the middle modular section (e.g., insertion module), to accommodate additional components (e.g., elevator mechanisms and the like). In other examples, wherein modular endoscope 100 is configured as an end-viewing device (e.g., gastroscope, colonoscope, cholangioscope, etc.), the distal modular section (e.g., camera module) can be generally co-axially positioned along a longitudinal axis of the middle modular section (e.g., insertion module).

Figure 6A:
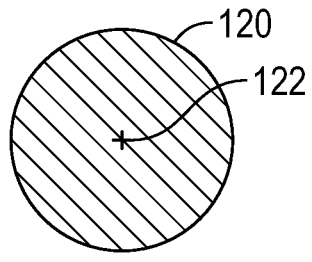
FIG. 6A is a schematic cross-sectional view of the insertion section module of FIG. 5 comprising a solid shaft.

FIG. 6A is a schematic cross-sectional view of an example of insertion section module 104 of FIG. 5 comprising solid shaft 120. Solid shaft 120 can comprise a flexible, elongate body that can couple navigation and control module 106 with functional module 102. Solid shaft can be comprised of any suitable material having suitable combinations of rigidity and flexibility for transmitting functional module 102 to the target anatomical region. In examples, solid shaft 120 can be fabricated from various polymers. In the illustrated example, solid shaft 120 comprises a circular cross-section centered on axis 122. In other examples, solid shaft 120 can have other cross-sectional profiles, such as rectilinear and polygonal.

Figure 6B:
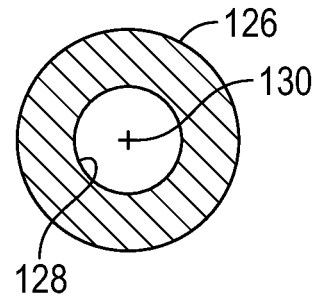
FIG. 6B is a schematic cross-sectional view of the insertion section module of FIG. 5 comprising a tubular body with a single lumen.

FIG. 6B is a schematic cross-sectional view of insertion section module 104 of FIG. 5 comprising tubular body 126 with lumen 128. Tubular body 126 can be configured similarly as solid shaft 120 but for the inclusion of lumen 128. Lumen 128 can comprise the only lumen within tubular body 126. In the illustrated example, lumen 128 can be centered along center axis 130. Lumen 128 can have a cross-sectional profile that matches the cross-sectional profile of the outer shape of tubular body 126 such that tubular body 126 can have uniform wall thickness. In other examples, lumen 128 can be offset from axis 130 such that the wall thickness of tubular body 126 is non-uniform.

Figure 6C:
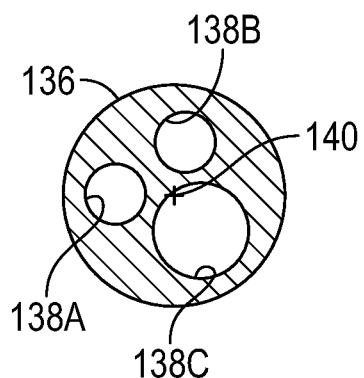
FIG. 6C is a schematic cross-sectional view of the insertion section module of FIG. 5 comprising a tubular body with a plurality of lumens.

FIG. 6C is a schematic cross-sectional view of insertion section module 104 of FIG. 5 comprising tubular body 136 with lumens 138A, 138B and 138C. Tubular body 126 can be configured similarly as solid shaft 120 but for the inclusion of lumens 128A-128C. Lumens 128A-128C can comprise a plurality of lumens extending through tubular body 136. In the illustrated example, tubular body 136 includes three lumens. In other examples, tubular body can comprise two lumens or more than three lumens. In the illustrated example, lumens 128A and 128B have the same cross-sectional profile and are smaller than the cross-sectional profile of lumen 128C. The number, cross-sectional shape and relative sizes of lumens within tubular body 136 can vary in different examples. However, the various examples can include a plurality of separate lumens each configured receive a separate component, e.g., wiring, fiber optics, fluid tubes and the like. As such, in the various examples, each of the plurality of lumens can be isolated from each other. In examples, lumens 138A-138C can be offset from axis 140 such that the wall thicknesses of tubular body 136 are non-uniform.

Figure 7:
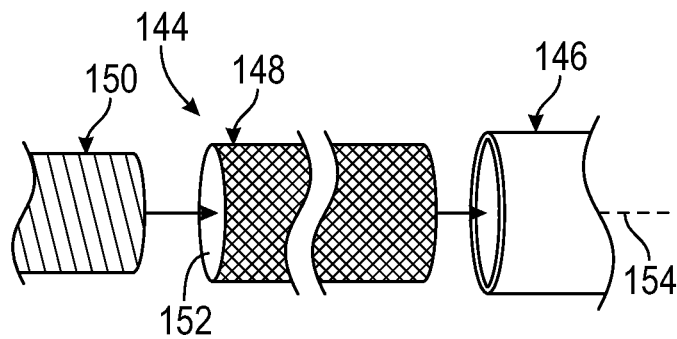
FIG. 7 is a schematic exploded view of the insertion section module of FIG. 5 comprising an outer tubing, a wire mesh tubing and a spiral band tubing.

FIG. 7 is a schematic exploded view of insertion section module 104 of FIG. 5 comprising tube sheath 144. Tube sheath 144 can comprise outer tubing 146, wire mesh tubing 148 and spiral band tubing 150. In an example, outer tubing 146, wire mesh tubing 148 and spiral band tubing 150 can comprise a single integrated unit wherein outer tubing 146, wire mesh tubing 148 and spiral band tubing 150 are pre-assembled into unit defining lumen 152 extending along axis 154. In additional examples, outer tubing 146, wire mesh tubing 148 and spiral band tubing 150 can comprise individual components that can be assembled piecemeal. That is, one or any combination of two of outer tubing 146, wire mesh tubing 148 and spiral band tubing 150 can be selected and assembled together.

Outer tubing 146 can comprise a protective cover for other components of a modular endoscope, such as by providing a sheath for sliding over solid shaft 120, tubular body 126 and tubular body 136, for example. Outer tubing 146 can comprise a waterproof, biocompatible material defining a lumen for the insertion of other component of the modular endoscope, e.g., wiring, fiber optics, fluid tubes and the like. Outer tubing 146 can be used by itself as the exoskeleton for the modular endoscope. However, outer tubing 146 can be reinforced with one or both of wire mesh tubing 148 and spiral band tubing 150 depending on the use for which the modular endoscope is built.

Wire mesh tubing 148 can comprise a tubular body formed of individual strands or bundles of strands woven together to form a tube. In examples, wire mesh tubing 148 can be fabricated from metallic strands, such as stainless steel. Wire mesh tubing 148 can be used to provide reinforcement to outer tubing 146, such to provide extra stiffening properties.

Spiral band tubing 150 can comprise a tubular body formed of a strand of material wound spirally into a helix. The strand of material can comprise circular or rectilinear cross-sectional profiles. In examples, spiral band tubing 150 can be fabricated from a metallic strand, such as stainless steel. Spiral band tubing 150 can be used to provide reinforcement to outer tubing 146, such as to facilitate torque transmission through insertion section module 104. That is, spiral band tubing 150 can facilitate rotational movement about axis 154 applied proximate navigation and control module 106 to functional module 102. Insertion section module 104 can comprise two oppositely wound spiral band tubes to facilitate torque transfer in opposite rotational directions.

In an example, outer tubing 146, wire mesh tubing 148 and spiral band tubing 150 can be configured as is described in Pub. No. US 2018/0235440 to Okamoto, titled "Insertion Device," which is hereby incorporated in its entirety by this reference.

Figure 8:
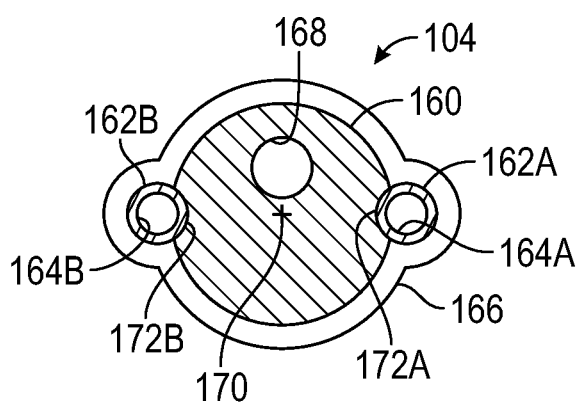
FIG. 8 is a schematic cross-sectional view of the insertion section module of FIG. 5 comprising a tubular body with tubes including lumens attached via a sleeve.

FIG. 8 is a schematic cross-sectional view of insertion section module 104 of FIG. 5 comprising tubular body 160 with tubes 162A and 162B including lumens 164A and 164B, respectively, attached via sleeve 166. Tubular body 160 can be configured similarly as solid shaft 120 but for the inclusion of lumen 168. In examples, tubular body 160 can further include indentations 172A and 172B that can be configured to mate with tubes 162A and 162B to reduce the overall size of insertion section module 104. Lumen 168 can be configured to be concentric with central axis 170 or can be offset from axis 170. Lumen 168 can have different cross-sectional profiles, including those that match the cross-sectional profile of tubular body 160 and those that are different.

Figure 9:
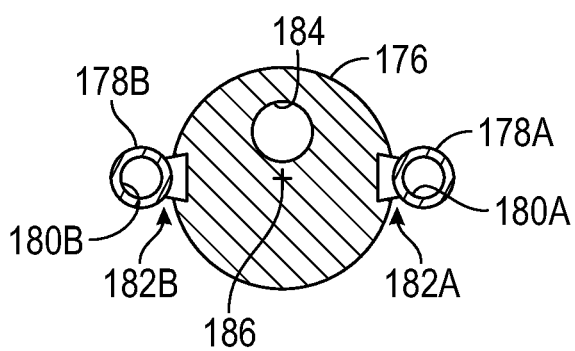
FIG. 9 is a schematic cross-sectional view of the insertion section module of FIG. 5 comprising a tubular body with tubes including lumens attached via mechanical fasteners.

FIG. 9 is a schematic cross-sectional view of insertion section module 104 of FIG. 5 comprising tubular body 176 with tubes 178A and 178B including lumens 180A and 180B, respectively, attached, via mechanical fasteners 182A and 182B. Tubular body 176 can be configured similarly as solid shaft 120 but for the inclusion of lumens 180A and 180B. Lumen 184 can be configured to be concentric with central axis 186 or can be offset from axis 186. Lumen 184 can have different cross-sectional profiles, including those that match the cross-sectional profile of tubular body 176 and those that are different. Fasteners 182A and 182B can be configured to attach tubes 178A and 178B to tubular body 176 in a releasable manner. Fasteners 182A and 182B can be configured as adjustable (e.g., tightenable) loops or straps into which tubes 178A and 178B are inserted. Fasteners 182A and 182B can be configured as tongue-and-groove or dovetail couplings wherein projections on one of tubular body 176 tubes 178A and 178B can be inserted into slots on the other of tubular body 176 tubes 178A and 178B. However, other types of mechanical fastening can be used.

Figure 10A:
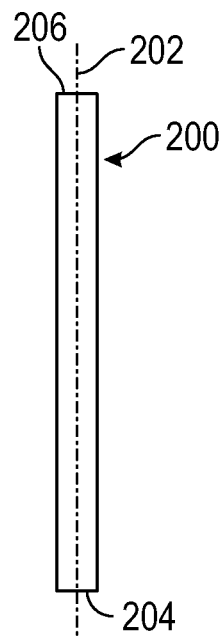
FIG. 10A is a schematic side view of the insertion section module of FIG. 5 comprising a straight shaft.

FIG. 10A is a schematic side view of insertion section module 104 of FIG. 5 comprising straight shaft 200. Straight shaft 200 can comprise any of solid shaft 120, tubular body 126, tubular body 136, tube sheath 144, tubular body 160 or tubular body 176. Straight shaft 200 can extend along central axis 202. Straight shaft 200 can be configured to extend from first end 204 to second end 206 in a linear manner without any curvature. As such, the natural or unbiased disposition of straight shaft 200 can be to extend in a linear manner without any outside influences.

Figure 10B:
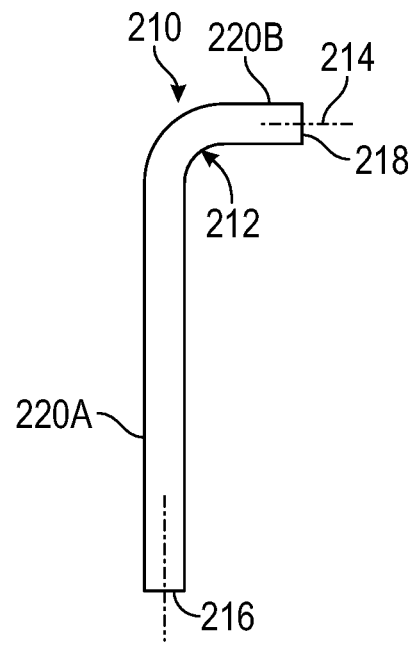
FIG. 10B is a schematic side view of the insertion section module of FIG. 5 comprising a shaft with a single pre-curve.

FIG. 10B is a schematic side view of insertion section module 104 of FIG. 5 comprising shaft 210 with single pre-curve 212. Shaft 210 can comprise any of solid shaft 120, tubular body 126, tubular body 136, tube sheath 144, tubular body 160 or tubular body 176. Shaft 210 can extend along central axis 214. Shaft 214 can be configured to extend from first end 216 to second end 218 in a bi-directional manner with a single curve. As such, the natural or unbiased disposition of shaft 210 can be that first shaft portion 220A can be configured to extend relative to second shaft portion 220B in an arcuate manner without any outside influences. In an example, second portion 220B can be configured to extend relative to first shaft portion 220A at a ninety-degree angle. Shaft 210 can be molded to have a pre-curve, or can include other components, such as springs or wires embedded within shaft 210 or attached to shaft 210 to provide the pre-curve.

Figure 10C:
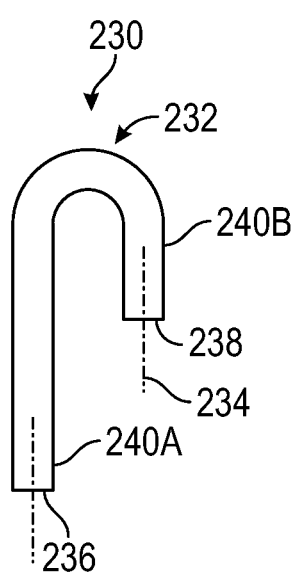
FIG. 10C is a schematic side view of the insertion section module of FIG. 5 comprising a shaft with a plurality of pre-curves.

FIG. 10C is a schematic side view of insertion section module 104 of FIG. 5 comprising shaft 230 with pre-curve 232. Shaft 230 can comprise any of solid shaft 120, tubular body 126, tubular body 136, tube sheath 144, tubular body 160 or tubular body 176. Shaft 230 can extend along central axis 234. Shaft 230 can be configured to extend from first end 236 to second end 238 in a multi-directional manner with a compound curve. As such, the natural or unbiased disposition of shaft 230 can be to such that first shaft portion 240A can be configured to extend relative to second shaft portion 240B in an arcuate manner without any outside influences. In an example, second portion 420B can be configured to extend relative to first shaft portion 240A at a one-hundred-eighty-degree angle. Shaft 230 can be molded to have a pre-curve, or can include other components, such as springs or wires embedded within shaft 210 or attached to shaft 210 to provide the pre-curve.

Figure 11A:
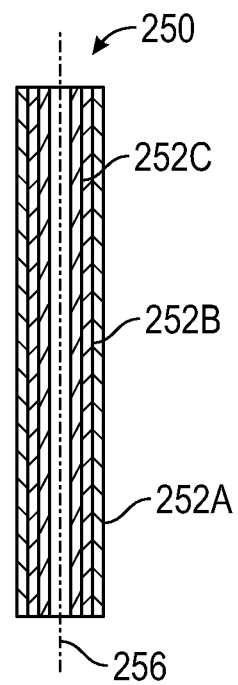
FIGS. 11A and 11B are schematic cross-sectional view of a telescoping shaft in a collapsed state and an extended state, respectively.
Figures 11B, 12:
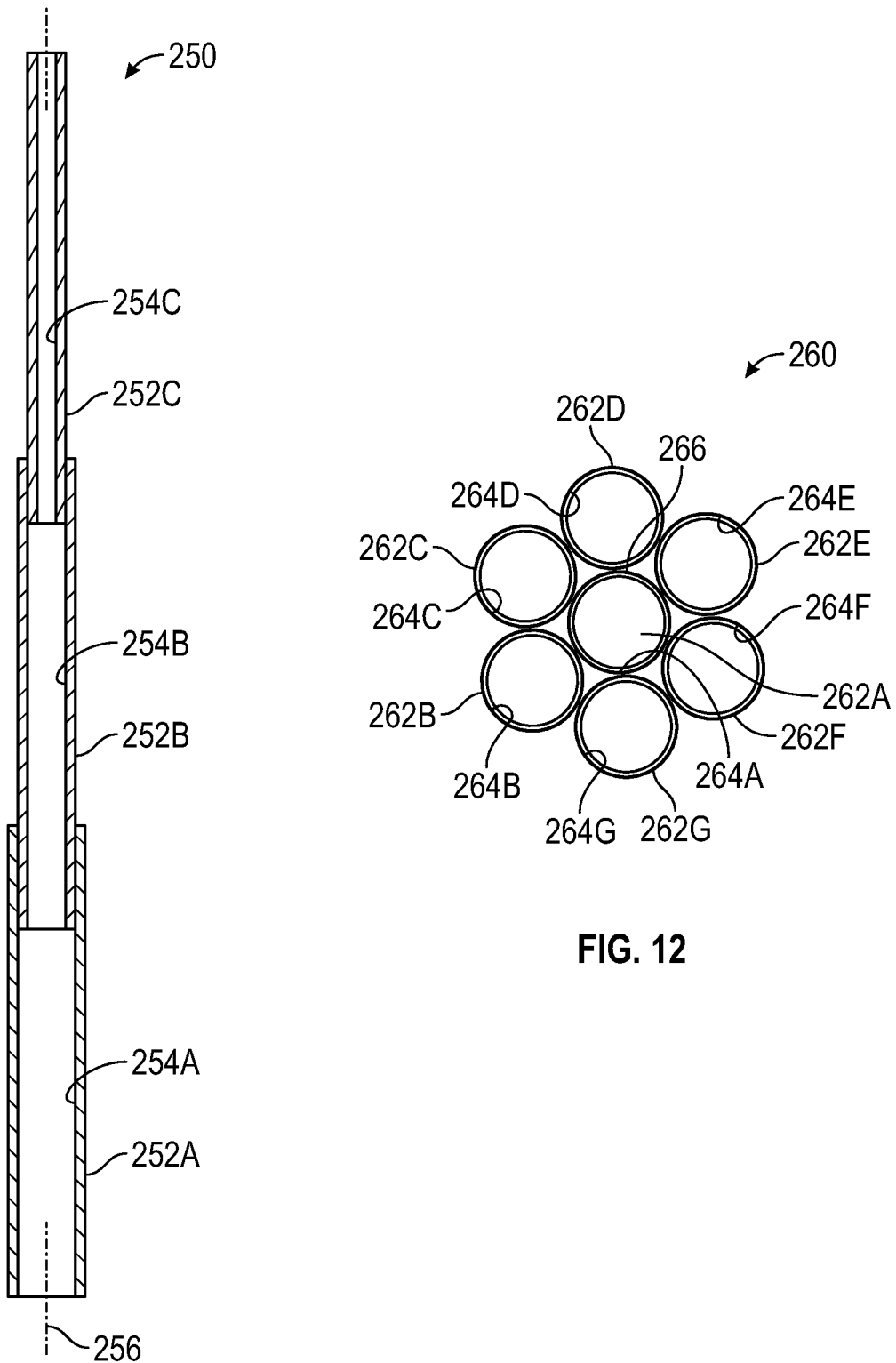
FIG. 12 is a schematic cross-sectional view of the insertion section module of FIG. 5 comprising a peelable bundle of tubular shafts.

FIGS. 11A and 11B are schematic cross-sectional view of insertion section module 104 of FIG. 5 comprising telescoping shaft 250 in a collapsed state and an extended state, respectively. Telescoping shaft 250 can comprise an outer shell comprising a plurality of segments including outer shaft 252A, middle shaft 252B and inner shaft 252C. Shafts 252A, 252B and 252C can comprise outer lumen 254A, middle lumen 254B and inner lumen 254C, respectively. Telescoping shaft 250 can be configured to axially expand to increase the total length of the device along axis 256. Shafts 252A, 252B and 252C can be configured to slide against each other. Specifically, inner shaft 252C can be configured to slide within lumen 254B and middle shaft 252B can be configured to slide within lumen 254A. Lumens 254A, 254B and 254C can be configured to align to so as to form a continuous elongate lumen extending through telescoping shaft 250 in the elongated configuration of FIG. 11B.

FIG. 12 is a schematic cross-sectional view of insertion section module 104 of FIG. 5 comprising peelable bundle 260 comprising outer shell comprising of tubular shafts 262A-262G. Shafts 262A-262G can include lumens 264A-264G, respectively. Shaft 262A can comprise a central shaft such that lumen 264A can extend along an axial center of peelable bundle 260. Shafts 262B-262G can be positioned around exterior 266 of shaft 262A and can be adhered thereto by any suitable means, such as adhesives, epoxies and the native stickiness of shafts 262A-262G. In additional examples, peelable bundle 260 can be inserted inside of a large lumen, such as lumen 128 of FIG. 6B, to sub-divide such lumen into smaller, segregated components. In such configurations, tubular shafts 262A-262G can be non-peelable, e.g., a bundle of unattached tubular shafts. FIG. 12 illustrates tubular shafts 262A-262G as all having the same diameter and cross-section. However, different diameters and cross-sectional shapes can be provided on each tubular shaft.

Figure 13A:
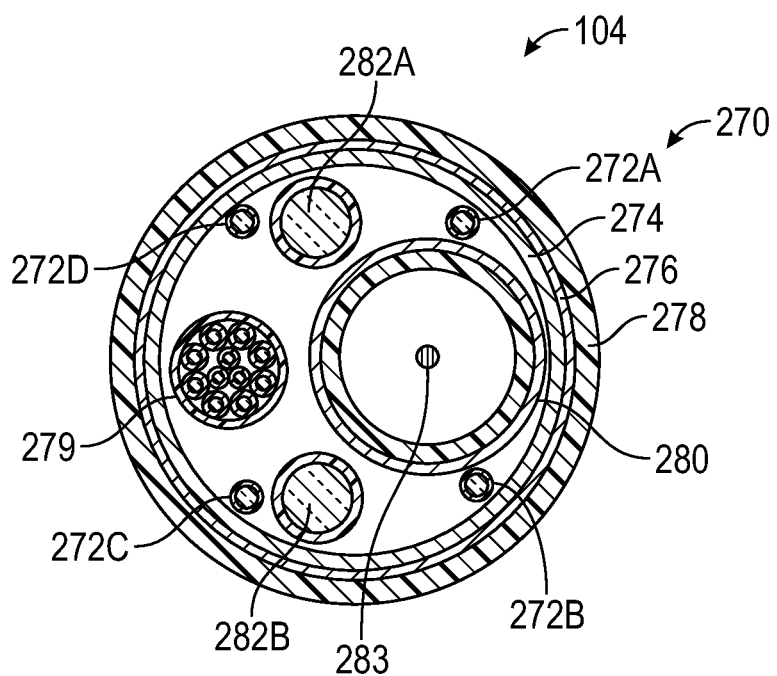
FIG. 13A is a schematic cross-sectional view of the insertion section module of FIG. 5 comprising pull wires.

FIG. 13A is a schematic cross-sectional view of the insertion section module 104 of FIG. 5 comprising steerable shaft 270 having pull wires or cables 272A-272D.

Steerable shaft 270 can comprise, for example, spiral sleeve 274, braid 276 covering an outer circumference of spiral sleeve 274 and outer covering 278 covering an outer circumference of braid 276. Steerable shaft 270 can further comprise image pickup cable 279, treatment instrument insertion channel 280 and pair of light guide cable 282A and 282B. Instrument insertion channel 280 can further comprise guide wire 283 over which another instrument, such as a catheter, can be inserted to be guided to the distal end of insertion channel 280.

In an example, Steerable shaft 270 can be configured as is described in Pub. No. US 2017/0224194 to Fujitani et al., titled "Endoscope," which is hereby incorporated in its entirety by this reference.

Figures 13B, 13C, 13D:
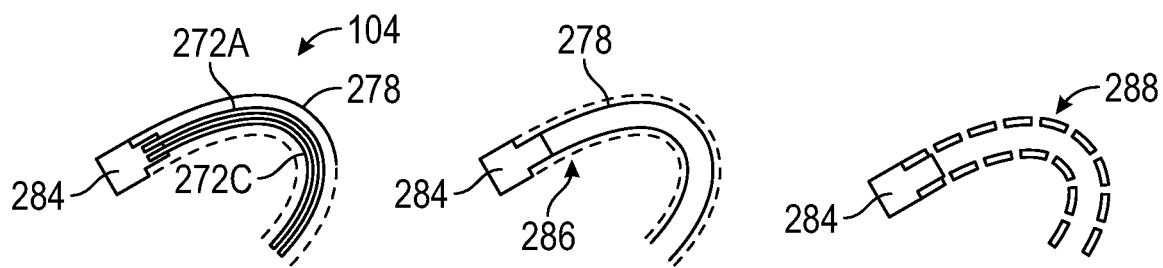
FIGS. 13B and 13C are schematic cross-sectional views of the insertion section module of FIG. 13A comprising a plurality of pull cables and a single pull cable, respectively.
FIG. 13D is a schematic cross-sectional view of the insertion section module of FIG. 13A comprising a flat wire spring with a pre-bend.

FIG. 13B is a schematic cross-sectional views of insertion section module 104 of FIG. 13A comprising a plurality of pull cables, including pull cables 272A-272D. Pull cables 272A-272D can be located within outer covering 278. One of pull cables 272A-272D can be provided for each direction that insertion section module 104 can be pulled in. As such, pull cables 272A-272D can be located circumferentially ninety degrees apart from each other relative to a central axis of insertion section module 104. Thus, insertion section module 104 can be pulled in four directions by pulling on individual pull cables 272A-272D. Also, insertion section module 104 can be pulled in directions between individual pull cables 272A-272D by pulling on adjacent pairs of pull cables 272A-272D. Pull cables 272A-272D can be coupled to cap 284. Cap 284 can comprise a simple anchor for securing pull cables 272A-272D or can comprise an operational functional or therapeutic module, such as functional module 102, endoscope camera module 50 and endoscope camera module 70.

FIG. 13C is a schematic cross-sectional views of insertion section module 104 of FIG. 5 comprising a single pull cable 272 with the addition of leaf spring 286. Leaf spring 286 can be configured to pre-curve or bend outer covering 278. In the configuration of FIG. 13C, leaf spring 286 can be provided opposite pull cable 272. As such, leaf spring 286 can axially bias outer covering 278 in one direction and pull cable 272 can be actuated, e.g., pulled, to overcome the bias of leaf spring 286 to straighten outer covering 278.

FIG. 13D is a schematic cross-sectional view of insertion section module 104 of FIG. 5 comprising flat wire spring 288 with pre-bend. Flat wire spring 288 can comprise a helically wound coil that wraps around the central axis of insertion section module 104 within outer covering 278. Flat wire spring 288 can be pre-curved or bent to provide directionality to insertion section module 104.

Flat wire spring 288, leaf spring 286 and pre-curved introduced into outer covering 278 can be used in conjunction with the example of FIGS. 10B and 10C.

FIGS. 14A and 14B are schematic cross-sectional view of insertion section module 104 of FIG. 5 comprising bendable shaft 300 in a collapsed state and an extended state, respectively. Bendable shaft 300 can comprise inner tube 302 and outer sheath 304. Inner tube 302 can comprise lumen 306 and exterior surface 308. Outer sheath 304 can be wrapped around inner tube 302. In various examples, inner tube 302 can comprise any of solid shaft 120, tubular body 126, tubular body 136, tube sheath 144, tubular body 160 or tubular body 176. Inner tube 302 can have biased or pre-disposed curvature 309, such with the example of FIGS. 10B and 10C. As such, the natural or unbiased disposition of inner tube 302 can be that first shaft portion 310A can be configured to extend relative to second shaft portion 310B in an arcuate manner along central axis 312 without any outside influences. Outer sheath 304 can envelope inner tube 302 to deflect or deform the bias of inner tube 302 into a straight configuration. As such, in FIG. 14A where outer sheath 304 is wrapped around inner tube 302, outer sheath 304 maintains inner tube 302 straight along central axis 312. Outer sheath 304 can be configured to be removed from inner tube 302, such as via ripping, tearing, tearing along a perforation, or sliding, to release the inherent tension of inner tube 302, thereby allowing inner tube 302 to flex back into its natural position of having a curvature, as shown in FIG. 14B.

FIGS. 15A and 15B are schematic cross-sectional view of insertion section module 104 of expandable shaft 320 in a collapsed state and an expanded state, respectively. Expandable shaft 320 can comprise an outer shell comprising inner tube 322 and outer sheath 324. Inner tube 322 can comprise lumen 326 and exterior surface 328. Outer sheath 324 can be wrapped around inner tube 322. In various examples, inner tube 322 can comprise any of solid shaft 120, tubular body 126, tubular body 136, tube sheath 144, tubular body 160 or tubular body 176. Inner tube 322 can have biased or pre-disposed bulbous portion 329. As such, the natural or unbiased disposition of inner tube 322 can be that first shaft portion 330A can be configured to extend straight along axis 332 and second shaft portion 330B can be configured to extend along axis 332 in a non-linear or curved manner to form interior chamber 334. Outer sheath 324 can envelope inner tube 322 to deflect or deform the bias of inner tube 322 into a straight configuration. As such, in FIG. 15A where outer sheath 324 is wrapped around inner tube 322, outer sheath 304 maintains inner tube 322 straight along central axis 332. Outer sheath 324 can be configured to be removed from inner tube 322, such as via ripping, tearing, tearing along a perforation, or sliding, to release the inherent tension of inner tube 322, thereby allowing inner tube 322 to flex back into its natural position of having bulbus portion 329, as shown in FIG. 15B.

Figure 16A:
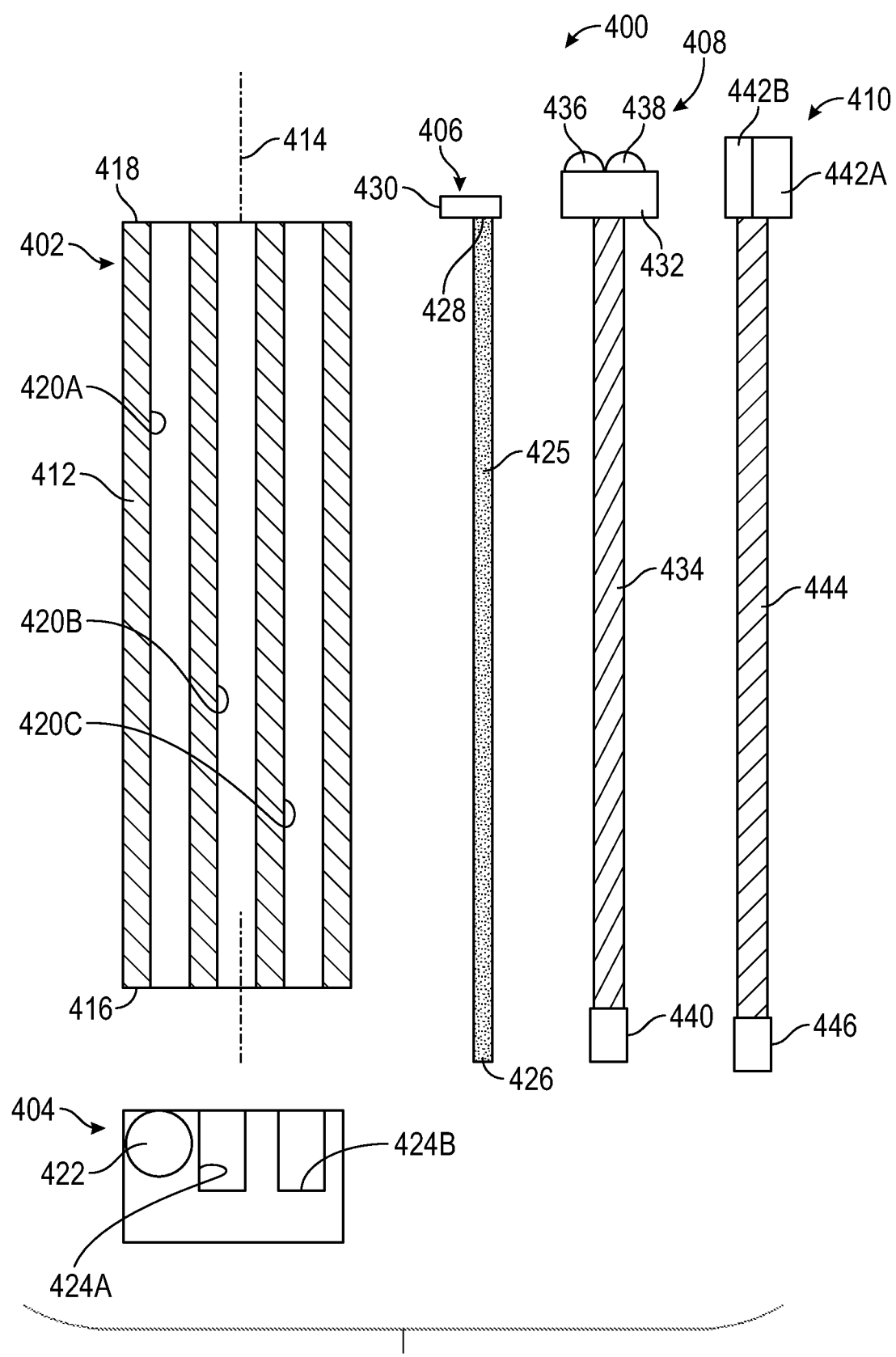
FIGS. 16A and 16B are schematic cross-sectional views of a first example of a modular endoscope comprising an exoskeleton, a control unit, a navigation unit, a camera unit, and a therapeutic unit in disassembled and assembled states, respectively.
Figure 16B:
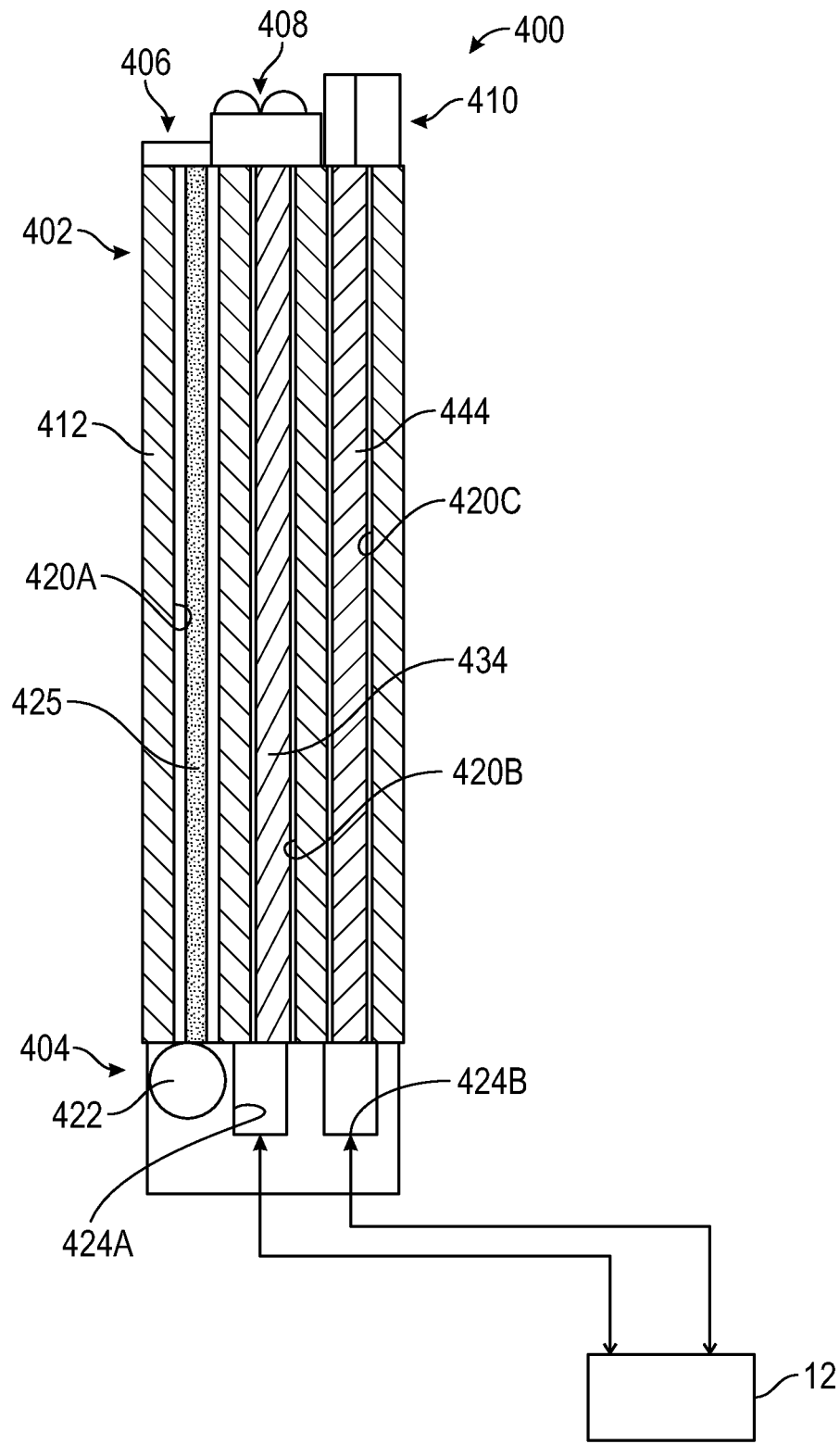

FIGS. 16A and 16B are schematic cross-sectional views of modular endoscope 400 comprising exoskeleton 402, control unit 404, navigation unit 406, camera unit 408, and therapeutic unit 410 in disassembled and assembled states, respectively. Modular endoscope 400 comprises a first example of an endoscope constructed according to the methods described herein, such as to be assembled with user-selected components to fulfill particular functions in performing a particular procedure on a specific-patient and then to be thereafter at least be partially deconstructed for selective disposal and reuse of individual components. In the example of FIGS. 16A and 16B, modular endoscope 400 comprises a steerable endoscope including therapeutic unit 410 that is configured as cutting forceps. FIGS. 16A and 16B are shown for illustrative purposes and are not shown to scale or in proportion to actual dimensions.

Exoskeleton 402 can comprise any of solid shaft 120, tubular body 126, tubular body 136, tube sheath 144, tubular body 160 or tubular body 176. In the illustrated embodiment, exoskeleton 402 comprises a multi-lumen shaft similar to that described with reference to tubular body 136 of FIG. 6C. Exoskeleton 402 can comprise elongate body 412 extending along axis 414 from proximal end 416 to distal end 418. Elongate body 412 can comprise lumens 420A, 420B and 420C. As such, exoskeleton 402 comprises a platform or structure inside which other components of modular endoscope 400 can be mounted.

Control unit 404 can comprise a handle, such as handle section 32 of FIG. 2. Control unit 404 can include features for interacting with navigation unit 406, camera unit 408 and therapeutic unit 410. For example, control unit 404 can comprise lever or wheel 422 for interacting with navigation unit 406. Additionally, control unit 404 can include sockets for receiving mating features of navigation unit 406, camera unit 408 and therapeutic unit 410. For example, control unit 404 can comprise electrical sockets 424A and 424B for receiving plugs 440 and 446 of camera unit 408 and therapeutic unit 410, respectively. Plugs 440 and 446 and sockets 424A and 424B can comprise any coupling system suitable for providing electric and/or fluid coupling, as well as mechanical coupling. In examples, threaded couplings can be used. In examples, control unit 404 can be attached to elongate body 412 with fasteners, such as with deflectable tabs or latches, or with threaded couplers.

Navigation unit 406 can comprise a steering wire 425 comprising proximal end 426 for connecting to wheel 422, and distal end 428 having catch 430 for connecting to distal end 418 of elongate body 412. Steering wire 425 can comprise a flexible wire, braid or bundle having sufficient tensile strength to pull catch 430 against distal end 418 to cause deflection of elongate body 412.

Camera unit 408 can comprise components for illuminating and capturing images of anatomy similar to those described with respect to FIGS. 3A-4B. Camera unit 408 can comprise housing 432, cable bundle 434, illumination lens 436 and objective lens 438. Housing 432 can include various lighting and imaging components, such as an imaging unit (CCD or CMOS), a prism and a light source. Illumination lens 436 can be coupled to the light source in housing 432 or can be coupled to a light transmitter, such as a fiber optic cable included in cable bundle 434. Objective lens 438 can be coupled to the imaging unit and the prism located in housing 432. Cable bundle 434 can include plug 440 for joining with socket 424A of control unit 404.

Therapeutic unit 410 can comprise forceps having jaws 442A and 442B. However, therapeutic unit 410 can be configured to provide other therapeutics. For example, therapeutic unit 410 can be configured as an ablation unit having one or more electrically activated electrodes, an acoustic unit having an ultrasound transducer, a cryogenic unit having fluid balloon or chamber, a cauterizing unit having heating element, a resecting or cutting unit having, e.g., one or more blades, a biologics collection unit, and an attaching unit having a stapler or the like. Therapeutic unit 410 can further comprise activation extension 444 and plug 446 for joining with socket 424B of control unit 404. Though the device of FIGS. 16A and 16B are illustrated with only on therapeutic module, other therapeutic and ancillary therapeutic modules can be attached by selecting an exoskeleton having additional lumens, or by using couplers 520 (FIGS. 17A and 17B) to attach additional modules outside of exoskeleton 402.

As can be seen in FIG. 16A, modular endoscope 400 can be comprised of individual, standalone components that have been selected from menus of options, such as those shown in FIGS. 18-21. Once selected, the individual components can be assembled together in a cohesive functioning unit, as shown in FIG. 16B.

Steering wire 425 of navigation unit 406 can be inserted into lumen 420A from distal end 418 such that proximal end 426 of wire 425 penetrates lumen 420A at proximal end 416. Catch 430 can engage distal end 418 to provide an anchor for steering wire 425. Catch 430 can be affixed to elongate body 412 in any suitable manner. Proximal end 426 of wire 425 can be attached to wheel 422.

Cable bundle 434 of camera unit 408 can be inserted into lumen 420B from distal end 418 such that plug 440 of cable bundle 434 penetrates lumen 420B at proximal end 416. Housing 432 can engage distal end 418 to provide stabilization to lenses 436 and 438. Housing 432 can be affixed to elongate body 412 in any suitable manner.

Activation extension 444 of therapeutic unit 410 can be inserted into lumen 420C from distal end 418 such that plug 446 of activation extension 444 penetrates lumen 420C at proximal end 416. Jaws 442A and 442B can be located proximate distal end 418 of elongate body 412 and stabilized thereat in any suitable manner.

Control unit 404 can be affixed to proximal end 416 of elongate body 412 after coupling with proximate end 426 of wire 425, plug 440 and plug 446. As such, wheel 422 can be operated to pull wire 425 and thereby flex elongate body 412. Signals can be transmitted to and from camera unit 408 through cable bundle 434 to control unit 404. Signals, electric, fluidic or mechanical, can be transmitted to and from therapeutic unit 410 to control unit 404. Control unit 404 can be coupled to imaging and control system 12 (FIG. 1).

Figure 17A:
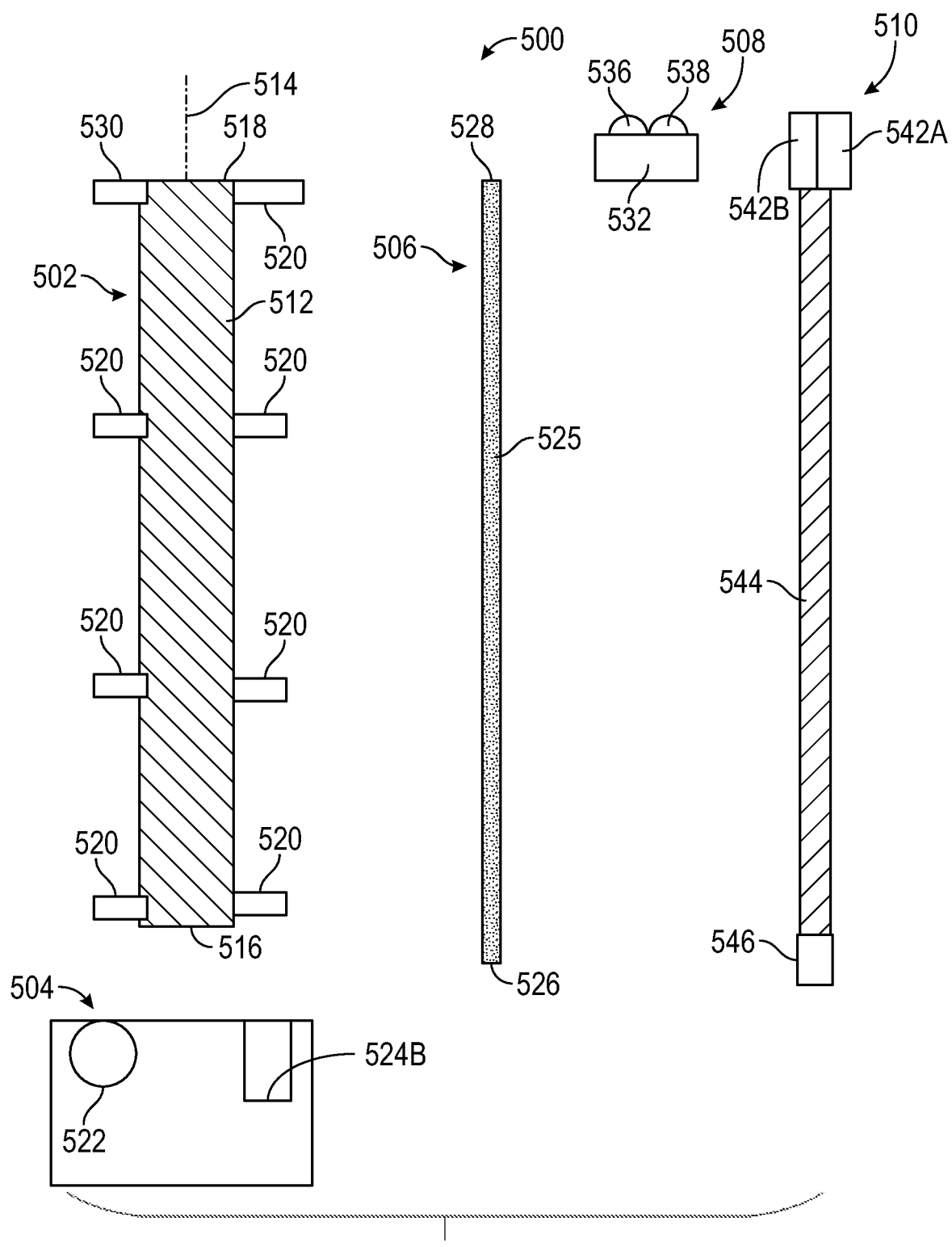
FIGS. 17A and 17B are schematic cross-sectional views of a second example of a modular endoscope comprising an exoskeleton, a control unit, a navigation unit, a camera unit, and a therapeutic unit in disassembled and assembled states, respectively.
Figure 17B:
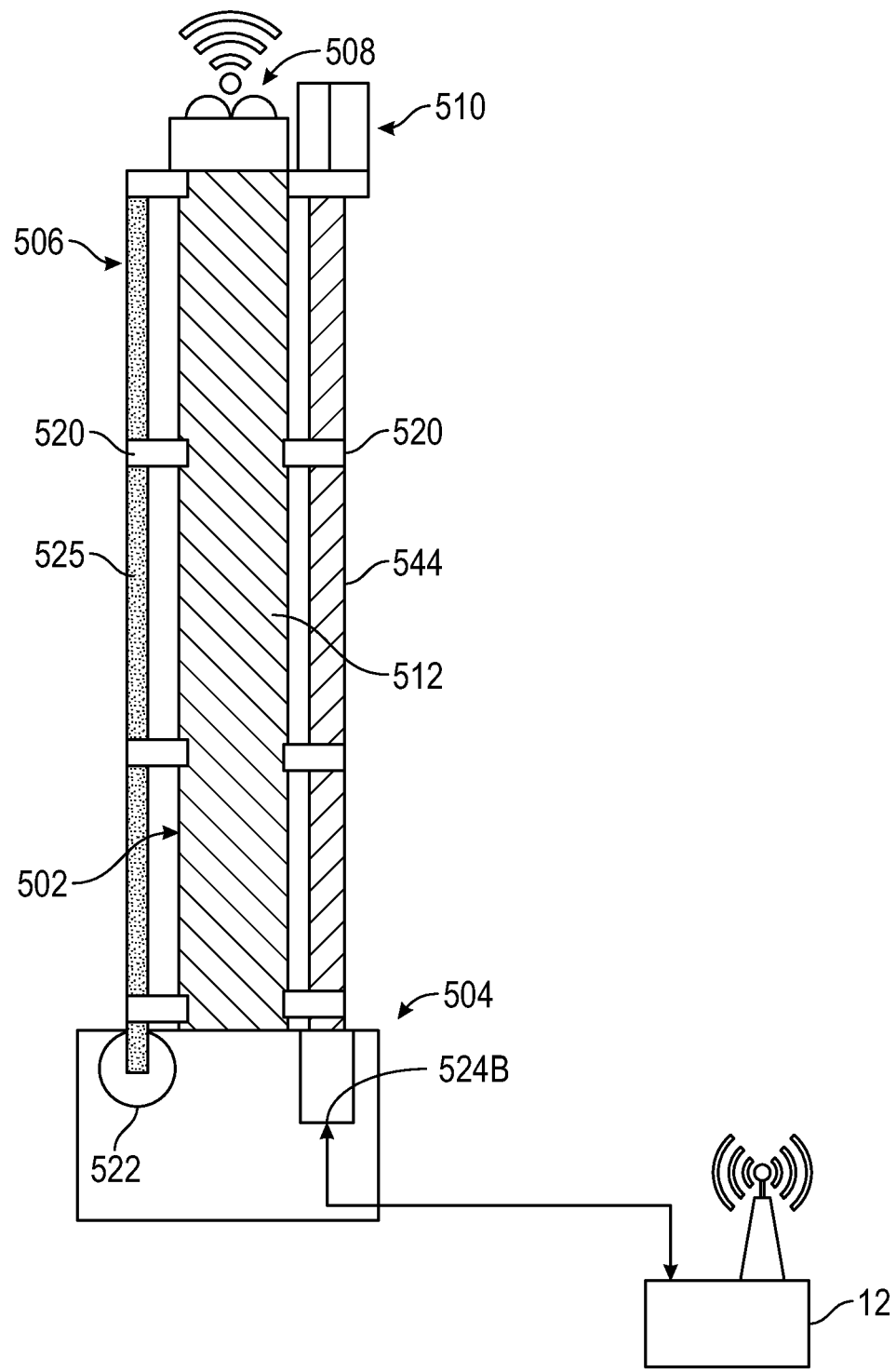

FIGS. 17A and 17B are schematic cross-sectional views of modular endoscope 500 comprising exoskeleton 502, control unit 504, navigation unit 506, camera unit 508, and therapeutic unit 510 in disassembled and assembled states, respectively. Modular endoscope 500 comprises a second example of an endoscope constructed according to the methods described herein, such as to be assembled with user-selected components to fulfill particular functions in performing a particular procedure on a specific-patient and then to be thereafter at least be partially deconstructed for selective disposal and reuse of individual components. In the example of FIGS. 17A and 17B, modular endoscope 500 comprises a steerable endoscope including therapeutic unit 510 that is configured as cutting forceps. FIGS. 17A and 17B are shown for illustrative purposes and are not shown to scale or in proportion to actual dimensions.

Endoscope 500 can comprise similar components as endoscope 400 except that navigation unit 506 and therapeutic unit 510 are disposed outside of elongate body 512 and camera unit 508 comprises a wireless module.

Exoskeleton 502 can comprise an elongate body 512 extending along axis 514 from proximal end 516 to distal end 518. Elongate body 512 can comprise a solid shaft without any lumens. In an example, exoskeleton 502 can comprise solid shaft 120 of FIG. 6A. As such, exoskeleton 502 comprises a platform or structure onto which other components of modular endoscope 500 can be mounted. In other examples, elongate body 512 can comprise lumens. Exoskeleton 502 can comprise couplers 520 that can be configured to attach components and modules to elongate body 512. Couplers 520 can comprise mechanical fasteners to facilitate attachment of components and modules to elongate body 512. In examples, couplers 520 can comprise tongue-and-groove couplers or dovetail. In additional examples, couplers 520 can comprise loops or straps providing passageways for the insertion of components and modules, such as steering wire 525 and activation extension 544.

Control unit 504 can be configured similarly as control unit 404 without socket 424A. Control unit 504 can comprise a handle, such as handle section 32 of FIG. 2. Control unit 504 can include features for interacting with navigation unit 506, camera unit 508 and therapeutic unit 510. For example, control unit 504 can comprise lever or wheel 522 for interacting with navigation unit 506. Additionally, control unit 504 can include sockets for receiving mating features of navigation unit 506, camera unit 508 and therapeutic unit 510. For example, control unit 504 can comprise electrical socket 524B for receiving plug 546 of therapeutic unit 510, respectively.

Navigation unit 506 can comprise a steering wire 525 comprising proximal end 526 for connecting to wheel 522, and distal end 528 for coupling to catch 530 for connecting to distal end 518 of elongate body 512. Steering wire 525 can comprise a flexible wire, braid or bundle having sufficient tensile strength to pull catch 530 against distal end 518 to cause deflection of elongate body 512.

Camera unit 508 can comprise components for illuminating and capturing images of anatomy similar to those described with respect to FIGS. 3A-4B. Camera unit 508 can comprise housing 532, illumination lens 536 and objective lens 538. Housing 532 can include various lighting and imaging components, such as an imaging unit (CCD or CMOS), a prism and a light source. Illumination lens 536 can be coupled to the light source in housing 532. Objective lens 538 can be coupled to the imaging unit and the prism located in housing 532. In examples, camera unit 508 can comprise a self-contained, sealed camera module configure for wireless communication with control unit 504 or imaging and control system 12 of FIG. 1. As such, camera unit 508 can comprise a wireless communication device, such as devices compliant with Institute of Electrical and Electronics Engineers (IEEE) 802.11 family of standards known as Wi-Fi®, IEEE 802.16 family of standards known as WiMax®, IEEE 802.15.4, Bluetooth devices, and the like. Likewise, imaging and control system 12 can be configured with a wireless transceiver.

Therapeutic unit 510 can comprise forceps having jaws 542A and 542B. However, therapeutic unit 510 can be configured to provide other therapeutics. For example, therapeutic unit 510 can be configured as an ablation unit having one or more electrically activated electrodes, an acoustic unit having an ultrasound transducer, a cryogenic unit having fluid balloon or chamber, a cauterizing unit having heating element, a resecting or cutting unit having, e.g., one or more blades, a biologics collection unit, and an attaching unit having a stapler or the like. Therapeutic unit 510 can further comprise activation extension 544 and plug 546 for joining with socket 524B of control unit 504.

As can be seen in FIG. 17A, modular endoscope 500 can be comprised of individual, standalone components that have been selected from menus of options, such as those shown in FIGS. 18-21. Once selected, the individual components can be assembled together in a cohesive functioning unit, as shown in FIG. 17B, in a similar manner as is explained with reference to FIGS. 16A and 16B, such as by using various fasteners, couplers and the like.

Figure 18:
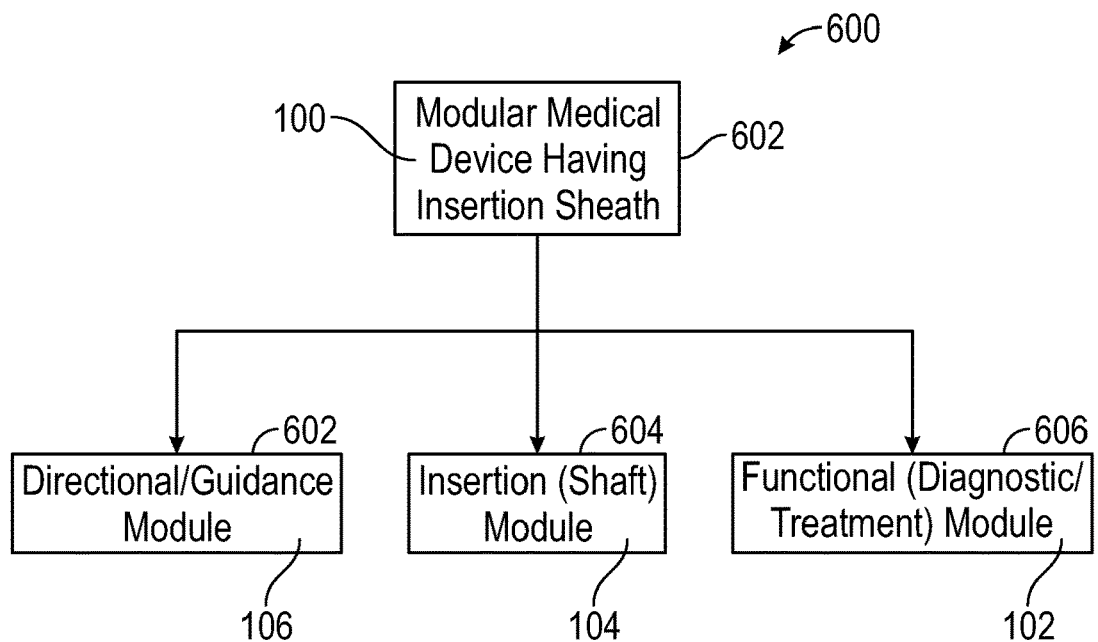
FIG. 18 is a schematic line diagram showing a method for building a modular endoscope comprising selecting a navigation and control module, an insertion module, and a functional module.

FIG. 18 shows a schematic line diagram showing a portion of method 600 for building modular endoscope 100 comprising selecting navigation and control module 106, insertion module 104, and functional module 102. The line diagram can comprise steps 602-608 of method 600 for designing modular endoscope 100 and can comprise a first menu screen for user-engagement. At step 602, a user can begin the design process. At steps 604, 606 and 608 a user can select any of navigation and control module 106, insertion module 104, and functional module 102 to begin constructing modular endoscope 100. Each of steps 604, 606 and 608 comprises a menu of options, that when engaged by a user, populates one or more lists of module options for a modular endoscope that can be constructed to build a custom-built endoscope for performing a procedure for a single patient, with some of the selected modules being disposable in various examples.

Figure 19:
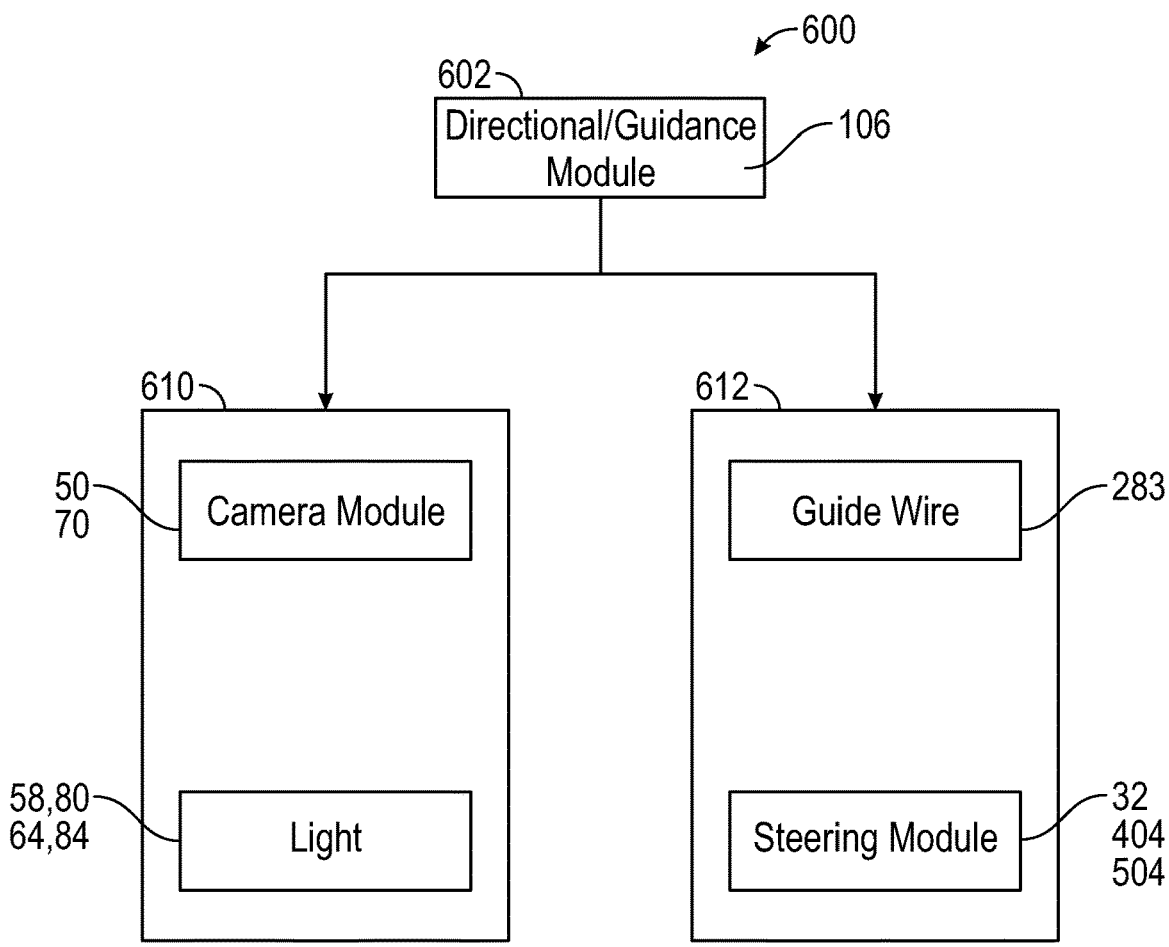
FIG. 19 is a schematic line diagram showing components for building a modular navigation and control module.

FIG. 19 is a schematic line diagram showing a portion of method 600 comprising selecting components for building modular navigation and control module 106. The line diagram can comprise steps 610-612 of method 600 for designing modular endoscope 100 and can comprise a second menu screen for user-engagement. Step 610 can comprise selecting imaging components, such as camera modules 50 and 70, for imaging anatomy and selecting lighting components, such as lens 58 and light transmitter 64, and lens 80 and light transmitter 84, for illuminating anatomy. Step 612 can comprise selecting components for steering exoskeletons discussed herein, such as handle section 32 and control units 404 and 504, and components for guiding other components through the selected exoskeleton, such as guide wire 283.

Figure 20A:
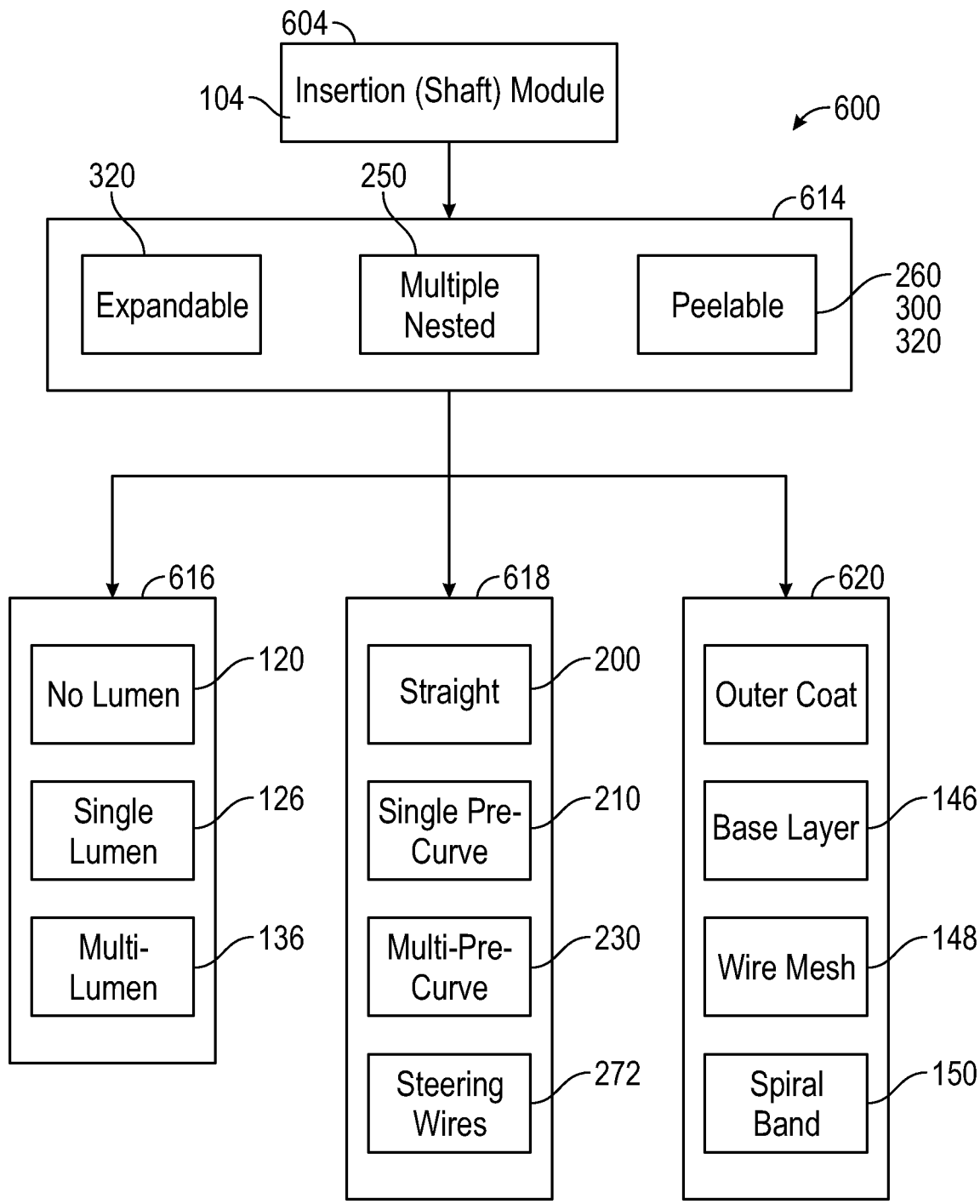
FIG. 20A is a schematic line diagram showing components for building a modular insertion module including modifiable exoskeletons, exoskeletons with lumens, curved exoskeletons, and reinforced exoskeletons.

FIG. 20A is a schematic line diagram showing a portion of method 600 comprising selecting components for building modular insertion module 104. The line diagram can comprise steps 614-620 of method 600 for designing modular endoscope 100 and can comprise a third menu screen for user-engagement. Step 604 can comprise step 614 for selecting dynamic shaft components, such as expandable shaft 320, nested shaft 250, and peelable shafts 300, 320 and 260. Step 616 can comprise selecting the number of lumens to be within the shaft, such as no lumens of solid shaft 120, a single lumen of tubular body 126, or multiple lumens of tubular body 136. Step 618 can comprise selecting the shape of the shaft to be used for insertion module 104, such as a straight shaft 200, single-curve shaft 210 and multi-curve shaft 230. Step 618 can additionally include selecting a number of steering wires or cables 272, if any, used to induce curvature or straightening of the selected shaft. Step 620 can comprise selecting components for sheathing of the selected shaft, such as outer tubing 146, wire mesh tubing 148 and spiral band tubing 150. Step 620 can also comprise selecting coatings, if any, to apply to the outside of the selected shaft, such as coatings used to improve sliding or reduce friction, lubricate, provide therapeutics and the like.

Figure 20B:
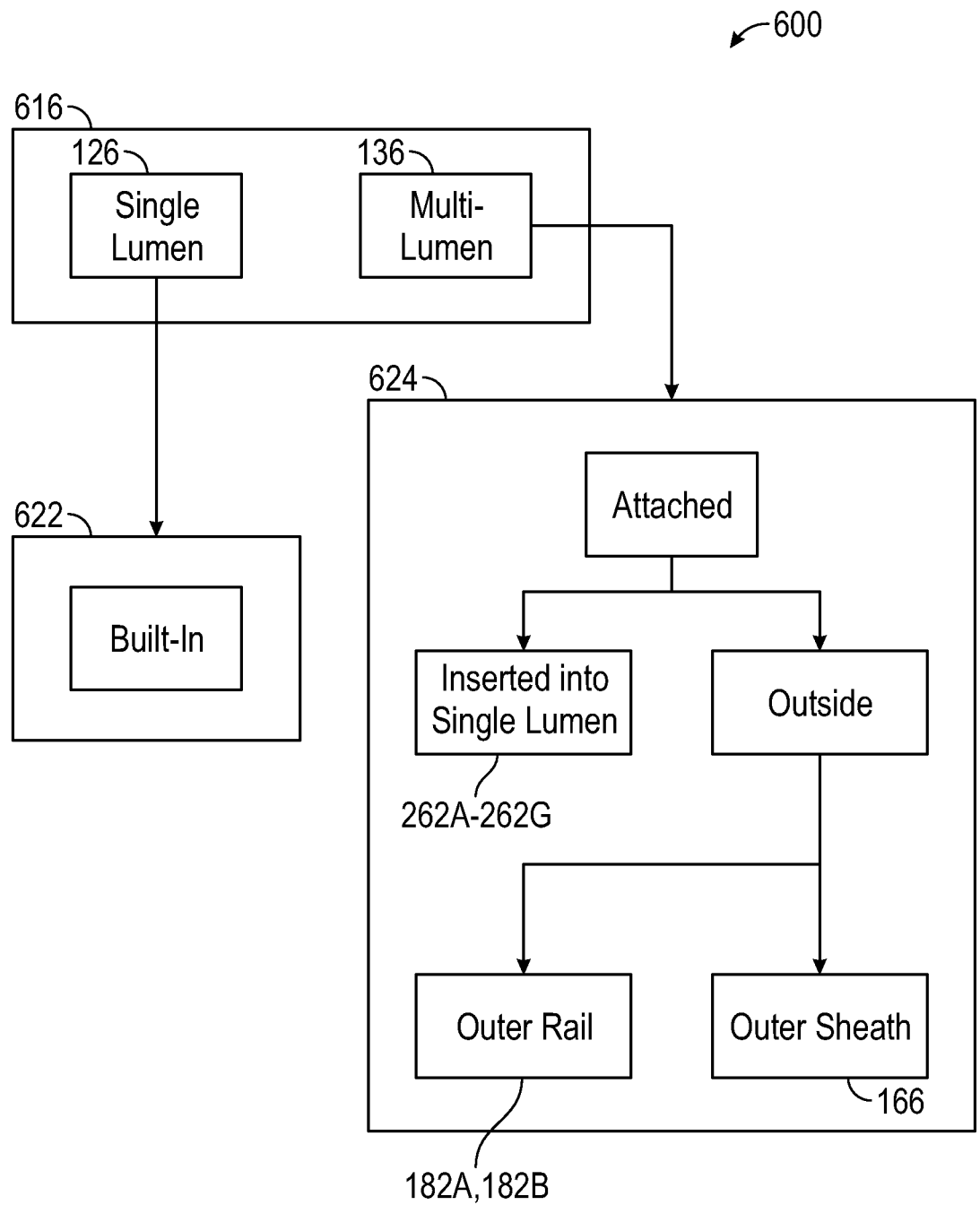
FIG. 20B is a schematic line diagram showing components for building exoskeletons with lumens via attached or integrated lumens.

FIG. 20B is a schematic line diagram showing a portion of method 600 comprising selecting components for building modular insertion module 104, such as by selecting exoskeletons configured for attaching modular components via attached or integrated lumens. The line diagram can comprise steps 622-624 of method 600 for designing modular endoscope 100 and can comprise a fourth menu screen for user-engagement. Step 622 can comprise selecting integrated lumens, such as integrated lumens 128, 138A-138C. Step 624 can comprise selecting attached lumens that are internally attached or externally attached. Internally attached lumens can comprise, for example, tubular shafts 262A-262G. Externally attached lumens can comprise, for example, lumens 164A and 164B and 180A and 180B.

Figure 21:
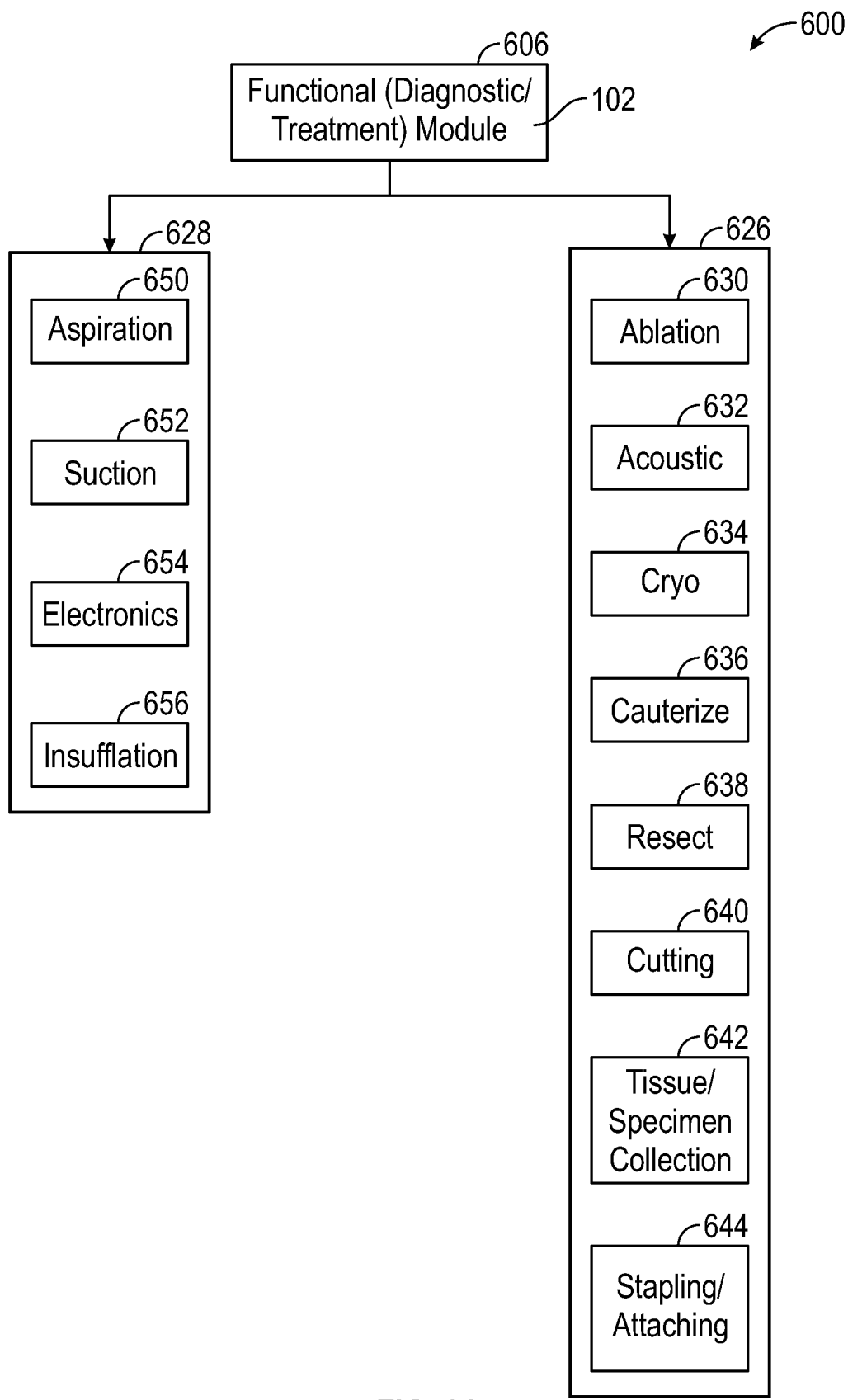
FIG. 21 is a schematic line diagram showing components for building a modular functional module.

FIG. 21 is a schematic line diagram showing a portion of method 600 comprising components for building a modular functional module 102. The line diagram can comprise steps 626-628 of method 600 for designing modular endoscope 100 and can comprise a fifth menu screen for user-engagement. Step 626 can comprise selecting treatment modules used to interact with anatomy of a patient. Step 628 can comprise selecting ancillary therapeutic modules. Treatment modules can comprise ablation module 630, acoustic module 632, cryogenic module 634, cauterization module 636, cauterization module 638, cutting module 640, collection module 642 and attaching module 644. Ancillary therapeutic modules can comprise aspiration module 650, suction module 652, electronics module 654 and insufflation module 656.

Figure 22:
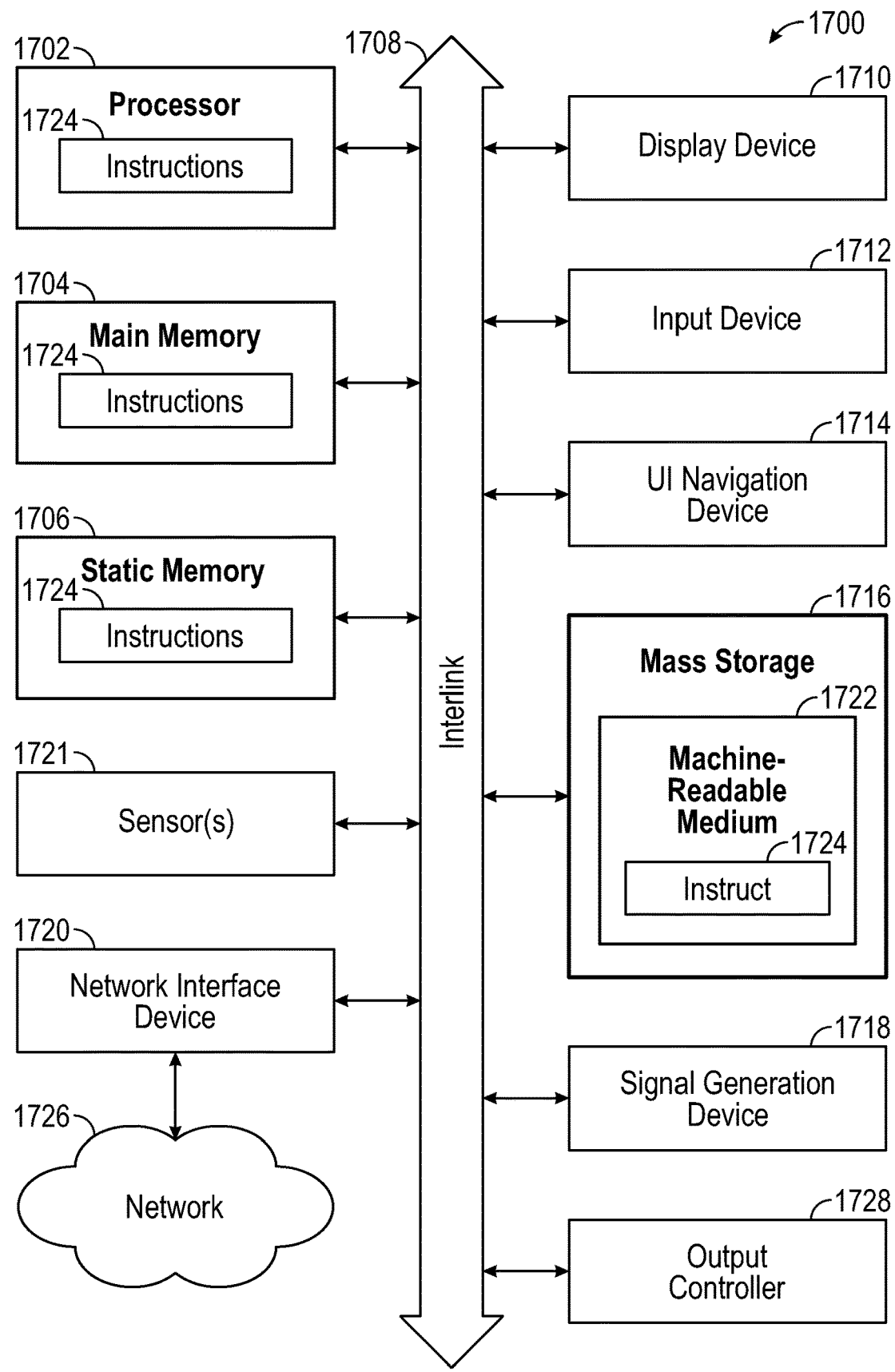
FIG. 22 is a block diagram of an example machine upon which any one or more of the techniques discussed herein may be performed and with which any of the devices discussed herein may be used in accordance with some embodiments.

FIG. 22 illustrates a block diagram of an example machine 1700 or planning system upon which any one or more of the techniques discussed herein may be performed in accordance with some embodiments. For example, machine 1700 can comprise a computing system, including a computing system connected to imaging and control system 12 of FIG. 1. Machine 1700 can comprise an example of a controller for endoscopy system 10 and a controller for designing a modular endoscope. As such instructions 1724 can be executed by processor 1702 to present and combine modular components of various modular endoscopes described herein. For example, various user-interfaceable graphical representations of the line diagrams can be presented on display device 1710. Thus, information regarding the different modular endoscope components can be stored in main memory 1704 and accessed by processor 1702. Main memory 1704 can additionally include inventory information for manufacturers and healthcare facilitators of modular endoscope components. Processor 1702 can also receive input (such as at input device 1712) relating to the selection of modular endoscope components selected by a healthcare provider, such as a surgeon, to perform a patient-specific procedure. Main memory 1704 can further include instructions regarding assembly and compatibility of individual components and modules such that instructions 1724 can be executed by processor 1702 to display such information on display device 1710.

In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 1716 may include machine readable medium 1722 on which is stored one or more sets of data structures or instructions 1724 (e.g., software) embodying or utilized by any one or more of the techniques or functions described herein. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks) or one or more antennas to connect to communications network 1726. In an example, network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

Figure 23:
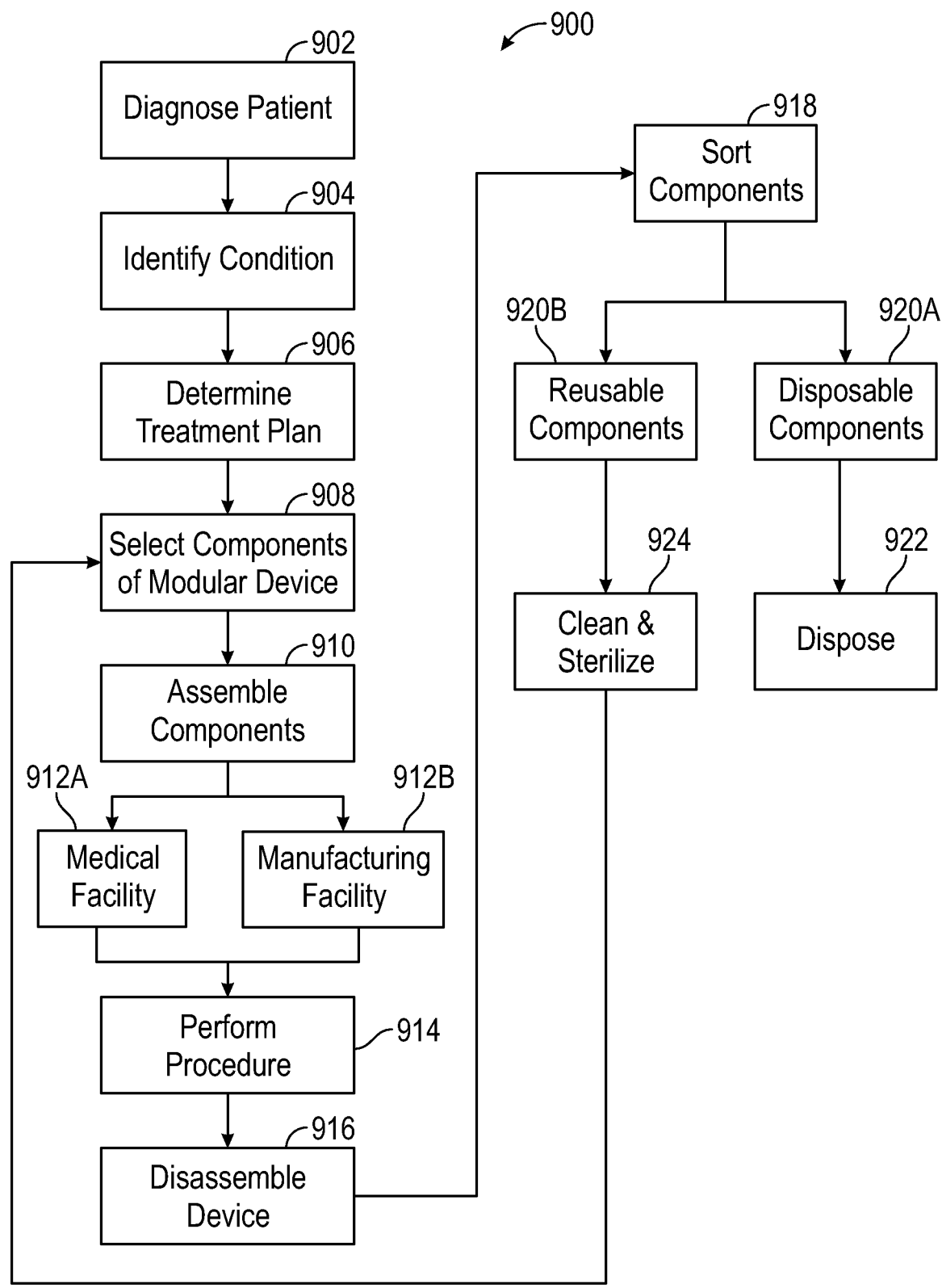
FIG. 23 is a block diagram illustrating a method of processing modular endoscope components for performing a surgical procedure.

FIG. 23 is a block diagram illustrating method 900 of processing modular endoscope components for performing a surgical procedure. At step 902, a specific patient can be diagnosed as having a particular condition or as needing a particular evaluation. A surgeon or other qualified medical professional can perform the diagnosis.

At step 904, a particular condition of the patient can be identified as needing interaction from a particular therapy or evaluative procedure. For example, a particular organ or anatomic region can be identified as needing a specific intervention or evaluation.

At step 906, a particular treatment plan can be developed to address the condition identified at step 904. The treatment plan can include selection of a therapy to be performed, such as ablation, freezing, cauterizing, cutting, attaching and the like.

At step 908, components of a medical device to deliver the selected therapy can be selected. For example, a particular treatment module can be selected to provide the selected therapy, a particular sheath or shaft can be selected to deliver the treatment module, and a particular control module can be selected to control operation of the modular medical device. Features and characteristics of the selected sheath or shaft can be selected, such as the number of delivery lumens needed to provide the treatment, guidance and steering capabilities needed for the selected treatment plan and therapy.

At step 910, the selected components of step 908 can be assembled. The selected components can be assembled at a medical facility where the procedure is to be performed, at step 912A. The selected components can be assembled at a manufacturing facility, at step 912B.

At step 914, the procedure planned for at step 906 can be performed with the medical device assembled at step 910.

At step 916, the assembled medical device used in the procedure at step 914 can be disassembled. The medical device can be disassembled at the medical facility of step 912A or can be sent offsite to be disassembled at the manufacturing facility of step 912B or another repurposing facility.

At step 918, the disassembled components can be sorted into components that can be disposed of at step 920A and components that can be reused at step 920B.

At step 922, the disposable components can be disposed of, such as by being destroyed or discarded.

At step 924, the reusable components of step 920B can be cleaned and sterilized for reuse. As such, the cleaned and sterilized components can be returned to inventory of the medical facility or manufacturing facility to be used in additional procedures.

Various Notes

Example 1 is a method for building a modular endoscope, the method comprising: determining a camera capability of the modular endoscope; determining a therapeutic capability of the modular endoscope; selecting an exoskeleton for the modular endoscope to be used with the determined camera and therapeutic capabilities of the modular endoscope; attaching a camera unit, if a camera capability is determined, to the selected exoskeleton to satisfy the determined camera capability; attaching a therapeutic unit, if a therapeutic capability is determined, to the selected exoskeleton to satisfy the determined therapeutic capability; and attaching a control unit to the exoskeleton to control any camera unit and therapeutic unit attached to the exoskeleton.

In Example 2, the subject matter of Example 1 optionally includes selecting one or more of a spiral band tubing, a wire mesh tubing and a polymeric outer tubing to surround the exoskeleton.

In Example 3, the subject matter of any one or more of Examples 1-2 optionally include wherein selecting the exoskeleton for the modular endoscope comprises determining a number of lumens included in the modular endoscope.

In Example 4, the subject matter of Example 3 optionally includes wherein selecting the exoskeleton for the modular endoscope comprises determining to include a single lumen with the modular endoscope.

In Example 5, the subject matter of any one or more of Examples 3-4 optionally include wherein selecting the exoskeleton for the modular endoscope comprises determining to include a plurality of lumens with the modular endoscope.

In Example 6, the subject matter of any one or more of Examples 3-5 optionally include wherein the included lumens extend extending through the exoskeleton.

In Example 7, the subject matter of Example 6 optionally includes wherein the included lumens are formed into a body of the exoskeleton.

In Example 8, the subject matter of any one or more of Examples 3-7 optionally include wherein the selected lumens are attached to an exterior of the exoskeleton.

In Example 9, the subject matter of Example 8 optionally includes wherein the selected lumens are attached to the exoskeleton via a tongue and groove connection.

In Example 10, the subject matter of any one or more of Examples 8-9 optionally include wherein the selected lumens are attached to the exoskeleton via a sheath.

In Example 11, the subject matter of any one or more of Examples 3-10 optionally include wherein selecting the exoskeleton for the modular endoscope comprises determining a number of lumens extending through the exoskeleton and determining a number of lumens to attach to the exoskeleton.

In Example 12, the subject matter of any one or more of Examples 3-11 optionally include wherein attaching the camera unit comprises: inserting a wire through a lumen included with the exoskeleton; and attaching a camera unit coupled to the wire to an end of the exoskeleton.

In Example 13, the subject matter of any one or more of Examples 1-12 optionally include wherein selecting the exoskeleton for the modular endoscope comprises selecting a solid flexible shaft.

In Example 14, the subject matter of any one or more of Examples 1-13 optionally include wherein attaching the camera unit comprises: attaching a wireless camera unit to an end of the exoskeleton.

In Example 15, the subject matter of any one or more of Examples 1-14 optionally include wherein the camera unit comprises a charge-coupled device (CCD) or a Complementary Metal Oxide Semiconductor (CMOS).

In Example 16, the subject matter of any one or more of Examples 1-15 optionally include wherein the camera unit further comprises a lighting unit.

In Example 17, the subject matter of any one or more of Examples 1-16 optionally include wherein selecting the exoskeleton for the modular endoscope comprises selecting an outer shell to surround the exoskeleton.

In Example 18, the subject matter of Example 17 optionally includes wherein selecting the outer shell comprises selecting a telescoping sheath.

In Example 19, the subject matter of any one or more of Examples 17-18 optionally include wherein selecting the exoskeleton comprises selecting an expandable exoskeleton to be surrounded by the outer shell.

In Example 20, the subject matter of any one or more of Examples 17-19 optionally include wherein selecting the outer shell comprises selecting one or more layers of a peelable outer shell.

In Example 21, the subject matter of any one or more of Examples 17-20 optionally include wherein selecting the exoskeleton for the modular endoscope comprises selecting a bundle of tubes.

In Example 22, the subject matter of any one or more of Examples 1-21 optionally include wherein selecting the exoskeleton for the modular endoscope comprises selecting an exoskeleton having a pre-curve.

In Example 23, the subject matter of Example 22 optionally includes wherein selecting the exoskeleton for the modular endoscope comprises selecting an exoskeleton having a plurality of pre-curves.

In Example 24, the subject matter of any one or more of Examples 1-23 optionally include determining a guidance or steering capability of the modular endoscope; and attaching a guidance or steering unit, if a guidance or steering capability is determined, to the selected exoskeleton to satisfy the determined guidance or steering capability.

In Example 25, the subject matter of Example 24 optionally includes wherein the guidance or steering unit comprises a guide wire.

In Example 26, the subject matter of any one or more of Examples 24-25 optionally include wherein the guidance or steering unit comprises at least one pull wire.

In Example 27, the subject matter of Example 26 optionally includes wherein the control unit includes a pull wire lever.

In Example 28, the subject matter of any one or more of Examples 1-27 optionally include wherein the therapeutic unit comprises one of an ablation unit, an acoustic unit, a cryogenic unit, a cauterizing unit, a resecting unit, a cutting unit, a biologics collection unit, and an attaching unit.

In Example 29, the subject matter of any one or more of Examples 1-28 optionally include determining an ancillary therapeutic capability of the modular endoscope; and attaching an ancillary therapeutic unit to the selected exoskeleton.

In Example 30, the subject matter of Example 29 optionally includes wherein the ancillary therapeutic unit comprises at least one of an aspiration unit, a suction unit, an insufflation unit, and an injection unit.

In Example 31, the subject matter of any one or more of Examples 1-30 optionally include coupling a communication link between the control unit and at least one of the camera unit and the therapeutic unit.

In Example 32, the subject matter of any one or more of Examples 1-31 optionally include wherein at least one of the camera unit, the therapeutic unit, and the control unit are releasably attached to the exoskeleton.

In Example 33, the subject matter of Example 32 optionally includes wherein the therapeutic unit is couplable by insertion into a lumen of the exoskeleton.

In Example 34, the subject matter of any one or more of Examples 31-33 optionally include wherein the control unit is threadedly engaged with the exoskeleton.

Example 35 is a modular endoscope system comprising: an exoskeleton; a camera unit couplable to the exoskeleton; a therapeutic unit couplable to the exoskeleton; a guidance or steering unit couplable to the exoskeleton; and a control unit couplable to the exoskeleton.

In Example 36, the subject matter of Example 35 optionally includes wherein the modular endoscope system comprises a set of exoskeletons from which the exoskeleton is selected, the set of exoskeletons comprising: an elongate solid shaft; an elongate tubular body defining a single lumen; and an elongate tubular body defining a plurality of lumens.

In Example 37, the subject matter of Example 36 optionally includes wherein the set of exoskeletons from which the exoskeleton is selected further comprises: a straight shaft; a shaft including a single pre-curve; and a shaft including a plurality of pre-curves.

In Example 38, the subject matter of any one or more of Examples 36-37 optionally include wherein the set of exoskeletons from which the exoskeleton is selected further comprises: a telescoping shaft; an expandable shaft; and a peelable shaft.

In Example 39, the subject matter of Example 38 optionally includes wherein the peelable shaft comprises: an inner tube defining a lumen; and an outer sheath peelable away from the inner tube.

In Example 40, the subject matter of any one or more of Examples 38-39 optionally include wherein the peelable shaft comprises a bundle of tubes that each define a lumen, wherein individual tubes of the bundle of tubes are peelable from the bundle.

In Example 41, the subject matter of any one or more of Examples 36-40 optionally include wherein the modular endoscope system further comprises a set of exoskeleton sheathing components comprising: a spiral band tubing; a wire mesh tubing; and a polymeric outer tubing.

In Example 42, the subject matter of any one or more of Examples 36-41 optionally include a plurality of elongate tubes configured to be attached to an exterior of the exoskeleton.

In Example 43, the subject matter of Example 42 optionally includes wherein the exoskeleton further comprises a coupling system configured to secure each of the plurality of elongate tubes to the exterior of the exoskeleton.

In Example 44, the subject matter of Example 43 optionally includes wherein the coupling system comprises a plurality of dovetail coupling components that correspond to the plurality of elongate tubes.

In Example 45, the subject matter of any one or more of Examples 43-44 optionally include wherein the coupling system comprises a sheath configured to hold the plurality of elongate tubes against the exoskeleton.

In Example 46, the subject matter of any one or more of Examples 35-45 optionally include at least one of a set of pull wires configured to attach to the exoskeleton and a guidewire configured to be inserted into a lumen of the exoskeleton.

In Example 47, the subject matter of any one or more of Examples 35-46 optionally include wherein the modular endoscope system comprises a set of camera units from which the camera unit is selected, the set of camera units comprising: a charge-coupled device (CCD); a Complementary Metal Oxide Semiconductor (CMOS); a High Definition (HD) camera; and a low-resolution camera.

In Example 48, the subject matter of Example 47 optionally includes wherein the camera unit further comprises a lighting unit.

In Example 49, the subject matter of any one or more of Examples 35-48 optionally include wherein the camera unit comprises a fastener for securing to a distal end of the exoskeleton.

In Example 50, the subject matter of any one or more of Examples 35-49 optionally include wherein the camera unit comprises a wireless communication device.

In Example 51, the subject matter of any one or more of Examples 35-50 optionally include wherein the camera unit comprises a cable configured to extend alongside or within the exoskeleton.

In Example 52, the subject matter of any one or more of Examples 35-51 optionally include wherein the therapeutic unit comprises one of an ablation unit, an acoustic unit, a cryogenic unit, a cauterizing unit, a resecting unit, a cutting unit, a biologics collection unit, and an attaching unit.

In Example 53, the subject matter of any one or more of Examples 35-52 optionally include wherein the modular endoscope system comprises a set of therapeutic units from which the therapeutic unit is selected, the set of therapeutic units comprising: an ablation unit; an acoustic unit; a cryogenic unit; a cauterizing unit; a resecting unit; a cutting unit; a biologics collection unit; and an attaching unit.

In Example 54, the subject matter of any one or more of Examples 35-53 optionally include wherein the modular endoscope system further comprises an ancillary therapeutic unit comprising at least one of an aspiration unit, a suction unit, an insufflation unit, and an injection unit.

In Example 55, the subject matter of Example 54 optionally includes wherein the modular endoscope system comprises a set of ancillary therapeutic units from which the ancillary therapeutic unit is selected, the set of ancillary therapeutic units comprising: an aspiration unit; a suction unit; an insufflation unit; and an injection unit.

Example 56 is a method of processing modular endoscope components for performing a surgical procedure, the method comprising: identifying a specific patient to receive a specific treatment; selecting components of the modular endoscope to perform the specific treatment; treating the specific patient with the modular endoscope; and deconstructing the components of the modular endoscope into reusable and disposable components.

In Example 57, the subject matter of Example 56 optionally includes assembling the components of the modular endoscope at a surgical facility.

In Example 58, the subject matter of any one or more of Examples 56-57 optionally include assembling the components of the modular endoscope at a manufacturing facility.

In Example 59, the subject matter of any one or more of Examples 56-58 optionally include diagnosing the patient as having a specific condition.

In Example 60, the subject matter of any one or more of Examples 56-59 optionally include wherein identifying a specific treatment comprises determining a treatment plan and associated diagnostics or therapeutics to perform the specific treatment.

In Example 61, the subject matter of any one or more of Examples 56-60 optionally include disposing of the disposable components.

In Example 62, the subject matter of any one or more of Examples 56-61 optionally include cleaning and sanitizing the reusable components.

In Example 63, the subject matter of Example 62 optionally includes reusing the cleaned and sanitized reusable components in a subsequent medical procedure.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for building a modular endoscope, the method comprising:
   identifying a single specific patient to receive a specific treatment according to a diagnosis before performing a medical procedure including the specific treatment;
   determining whether or not at least one of a camera capability and a therapeutic capability will be used by the modular endoscope to perform the specific treatment considering the specific single patient after identifying the specific single patient and before performing the medical procedure, the camera capability comprising an ability of the modular endoscope to obtain imaging and transmit an imaging signal, the therapeutic capability comprising an ability of the modular endoscope to perform a therapeutic intervention;
   presenting a menu of options of a plurality of exoskeletons suitable for use as a shaft of the modular endoscope;
   selecting an exoskeleton from the menu of options of the plurality of exoskeletons for the modular endoscope to be used with the determined camera and therapeutic capabilities of the modular endoscope after identifying the specific single patient;
   attaching a camera unit, when a camera capability is determined to be used, to the selected exoskeleton to satisfy the determined camera capability after identifying the specific single patient and before performing the medical procedure;
   attaching a therapeutic unit, when a therapeutic capability is determined to be used, to the selected exoskeleton to satisfy the determined therapeutic capability after identifying the specific single patient and before performing the medical procedure; and attaching a control unit to the exoskeleton to control any camera unit and therapeutic unit attached to the exoskeleton after identifying the specific single patient and before performing the medical procedure.

2. The method of claim 1, further comprising selecting one or more of a spiral band tubing, a wire mesh tubing and a polymeric outer tubing to surround the exoskeleton.

3. The method of claim 1, wherein selecting the exoskeleton for the modular endoscope comprises:
determining a number of lumens included in the modular endoscope, wherein the included lumens extend extending through the exoskeleton.

4. The method of claim 3, wherein the included lumens are formed into a body of the exoskeleton.

5. The method of claim 3, wherein:
the selected lumens are attached to an exterior of the exoskeleton; and
the selected lumens are attached to the exoskeleton via a tongue and groove connection.

6. The method of claim 3, wherein:
the selected lumens are attached to an exterior of the exoskeleton; and
the selected lumens are attached to the exoskeleton via a sheath.

7. The method of claim 3, wherein selecting the exoskeleton for the modular endoscope comprises determining a number of lumens extending through the exoskeleton and determining a number of lumens to attach to the exoskeleton.

8. The method of claim 3, wherein attaching the camera unit comprises:
inserting a wire through a lumen included with the exoskeleton;
attaching a camera unit coupled to the wire to an end of the exoskeleton; and
attaching the control unit to the wire;
wherein attaching the control unit to the exoskeleton to control any camera unit and therapeutic unit attached to the exoskeleton before performing the medical procedure comprises attaching the control unit to the wire.

9. The method of claim 1, wherein selecting the exoskeleton for the modular endoscope comprises:
determining a number of lumens included in the modular endoscope, and
determining to include a single lumen with the modular endoscope.

10. The method of claim 1, wherein selecting the exoskeleton for the modular endoscope comprises:
determining a number of lumens included in the modular endoscope, and
determining to include a plurality of lumens with the modular endoscope.

11. The method of claim 1, wherein selecting the exoskeleton for the modular endoscope comprises selecting a solid flexible shaft.

12. The method of claim 1, wherein attaching the camera unit comprises:
attaching a wireless camera unit to an end of the exoskeleton, wherein the camera unit comprises a charge-coupled device (CCD) or a Complementary Metal Oxide Semiconductor (CMOS).

13. The method of claim 1, wherein the camera unit further comprises a lighting unit.

14. The method of claim 1, wherein:
selecting the exoskeleton for the modular endoscope comprises selecting an outer shell from the menu of options of the plurality of exoskeletons to surround the exoskeleton, wherein each of the plurality of exoskeletons is functionally different from each other; and
selecting the outer shell comprises selecting a telescoping sheath.

15. The method of claim 1, wherein:
selecting the exoskeleton for the modular endoscope comprises selecting an outer shell from the menu of options of the plurality of exoskeletons to surround the exoskeleton, wherein each of the plurality of exoskeletons is functionally different from each other; and
selecting the exoskeleton comprises selecting an expandable exoskeleton to be surrounded by the outer shell.

16. The method of claim 1, wherein:
selecting the exoskeleton for the modular endoscope comprises selecting an outer shell from the menu of options of the plurality of exoskeletons to surround the exoskeleton, wherein each of the plurality of exoskeletons is functionally different from each other; and
selecting the outer shell comprises selecting one or more layers of a peelable outer shell.

17. The method of claim 1, wherein:
selecting the exoskeleton for the modular endoscope comprises selecting an outer shell from the menu of options of the plurality of exoskeletons to surround the exoskeleton, wherein each of the plurality of exoskeletons is functionally different from each other; and
selecting the exoskeleton for the modular endoscope comprises selecting a bundle of tubes.

18. The method of claim 1, wherein selecting the exoskeleton for the modular endoscope comprises selecting an exoskeleton having at least one pre-curve.

19. The method of claim 1, further comprising:
determining whether or not a guidance or steering capability of the modular endoscope will be used to perform the specific treatment, the guidance or steering capability selected from a menu of options including various guidance or steering capabilities, each guidance or steering capability comprising a feature for bending or steering the exoskeleton; and
attaching a guidance or steering unit, when a guidance or steering capability is determined to be used, to the selected exoskeleton to satisfy the determined guidance or steering capability;
wherein the guidance or steering unit is attached separately from the camera unit.

20. The method of claim 19, wherein the guidance or steering unit comprises a guide wire.

21. The method of claim 19, wherein:
the guidance or steering unit comprises at least one pull wire;
the control unit includes a pull wire lever; and
the at least one pull wire is inserted into a lumen of the selected exoskeleton independent of a lumen for the camera unit and a lumen for the therapeutic unit.

22. The method of claim 1, wherein the therapeutic unit comprises one of an ablation unit, an acoustic unit, a cryogenic unit, a cauterizing unit, a resecting unit, a cutting unit, a biologics collection unit, and an attaching unit.

23. The method of claim 1, further comprising:
determining whether or not an ancillary therapeutic capability of the modular endoscope will be used to perform the specific treatment, the ancillary therapeutic capability selected from a menu of options including various ancillary therapeutic capabilities, each of the ancillary therapeutic capabilities comprising a different therapeutic device configured to treat or evaluate tissue; and attaching an ancillary therapeutic unit to the selected exoskeleton.

24. The method of claim 23, wherein the ancillary therapeutic unit comprises at least one of an aspiration unit, a suction unit, an insufflation unit, and an injection unit.

25. The method of claim 1, further comprising coupling a communication link between the control unit and at least one of the camera unit and the therapeutic unit.

26. The method of claim 25, wherein the camera unit and the control unit are threadedly engaged with the exoskeleton and the therapeutic unit is user-detachable from the exoskeleton.

27. The method of claim 1, wherein at least one of the camera unit and the control unit are releasably attached to the exoskeleton and the therapeutic unit is couplable to the exoskeleton by insertion into a lumen of the exoskeleton.

28. The method of claim 1, further comprising:
presenting a menu of options of a plurality of camera capabilities suitable for use with the modular endoscope, each of the plurality of camera capabilities comprising a different resolution for the imaging signal;
selecting the camera capability from the menu of options of the plurality of camera capabilities;
presenting a menu of options of a plurality of therapeutic capabilities suitable for use with the modular endoscope, each of the plurality of therapeutic capabilities comprising a different therapeutic device configured to treat or evaluate tissue; and
selecting the therapeutic capability from the menu of options of the plurality of therapeutic capabilities.

29. The method of claim 28, wherein the menu of options of the plurality of camera capabilities and the menu of options of the plurality of therapeutic capabilities are presented on a display screen of a user interface device.

30. The method of claim 1, further comprising utilizing a planning system machine to select components for building the modular endoscope, the planning system machine comprising:
a non-transitory computer readable medium having stored therein menus of options for constructing the modular endoscope, each menu of options comprising a list of specific modular endoscope components;
a display screen operatively connected to the non-transitory computer readable medium and configured to display the menus of options; and
a user interface device configured to allow a user to select options from the menus of options to build the modular endoscope.

31. The method of claim 1, further comprising building the modular endoscope with the exoskeleton, the control unit and at least one of the camera unit and the therapeutic unit after identifying the single specific patient and before performing the medical procedure.

32. The method of claim 1, wherein the specific treatment for the single specific patient is determined according to a treatment plan developed before the medical procedure is performed and before the modular endoscope is assembled.

33. The method of claim 1, wherein the modular endoscope is built at a first location remote from a second location where the medical procedure is to be performed, wherein the first location where the medical procedure is to be performed and the second location where the modular endoscope is built comprise different locations within a medical facility.

34. The method of claim 1, wherein the modular endoscope is built at a first location remote from a second location where the medical procedure is to be performed, wherein the first location where the modular endoscope is built comprises a manufacturing facility.

35. The method of claim 1, wherein attaching the camera unit, when the camera capability is determined to be used, to the selected exoskeleton to satisfy the determined camera capability before performing the medical procedure comprises attaching the camera unit to a distal-most end of the selected exoskeleton so as to be located distally of the selected exoskeleton.

36. The method of claim 1, wherein attaching the control unit to the exoskeleton to control any camera unit and therapeutic unit attached to the exoskeleton before performing the medical procedure comprises attaching the control unit to a proximal-most end of the selected exoskeleton so as to be located proximally of the selected endoscope.

37. The method of claim 1, wherein the control unit comprises a single handpiece for operating functionality of the camera unit and the therapeutic unit.

* * * * *